United States Patent
O'Heeron et al.

(10) Patent No.: US 11,878,037 B2
(45) Date of Patent: Jan. 23, 2024

(54) CONCURRENT ACTIVATION OF REGENERATIVE AND TOLEROGENIC PROCESSES BY FIBROBLAST-BASED COMPOSITIONS FOR THE TREATMENT OF MULTIPLE SCLEROSIS

(71) Applicant: Figene, LLC, Houston, TX (US)

(72) Inventors: Pete O'Heeron, Houston, TX (US); Thomas Ichim, San Diego, CA (US)

(73) Assignee: Figene, LLC, Houston, TX (US)

(*) Notice: Subject to any disclaimer, the term of this patent is extended or adjusted under 35 U.S.C. 154(b) by 737 days.

(21) Appl. No.: 16/887,720

(22) Filed: May 29, 2020

(65) Prior Publication Data

US 2020/0376041 A1    Dec. 3, 2020

Related U.S. Application Data

(60) Provisional application No. 62/855,010, filed on May 31, 2019.

(51) Int. Cl.
    *A61K 35/33*      (2015.01)
    *C12N 5/077*      (2010.01)

(52) U.S. Cl.
    CPC ............ *A61K 35/33* (2013.01); *C12N 5/0656* (2013.01); *C12N 2501/22* (2013.01); *C12N 2501/26* (2013.01)

(58) Field of Classification Search
None
See application file for complete search history.

(56) References Cited

U.S. PATENT DOCUMENTS

| | | | |
|---|---|---|---|
| 8,017,112 B2 * | 9/2011 | Li | A61P 25/28 435/377 |
| 8,679,834 B2 | 3/2014 | Lombardo et al. | |
| 2014/0322158 A1 | 10/2014 | Dhib-Jalbut | |
| 2017/0290864 A1 | 10/2017 | Wang et al. | |
| 2019/0072551 A1 | 3/2019 | Kuerten et al. | |
| 2019/0269736 A1 * | 9/2019 | Lafont | A61K 35/36 |
| 2021/0393700 A1 * | 12/2021 | O'Heeron | A61K 35/16 |

FOREIGN PATENT DOCUMENTS

| | | |
|---|---|---|
| WO | WO 2006/013107 | 2/2006 |
| WO | WO 2009/046377 | 4/2009 |

OTHER PUBLICATIONS

Bouffi et al, Ann Rheum Dis, 2011, 70: 1671-1676. (Year: 2011).*
Haniffa et al, J Immunol, 2007, 179:1595-1604. (Year: 2007).*
Jalili et al, PLoS One, 2016, 11(1): e0146970. (Year: 2016).*
Palkowitz et al, Adv Healthcare Mater, 2021, 2100132 (Year: 2021).*
Ghaffari et al., "Circulating concentrations of interleukin (IL)-17 in paitients with multiple sclerosis: Evaluation of the effects of gender, treatment, disease patterns and IL-23 receptor gene polymorphisms", Iran J Neurol 2017; 16(1): 15-25.
Extended European Search Report issued in European Patent Application No. 208156315, dated May 17, 2023.
Ichim et al., "Fibroblasts as a practical alternative to mesenchymal stem cells," Journal of Translational Medicine, 16(1), pp. 1-9, 2018.
Shagab et al., "Interleukin-17 in human inflammatory diseases," Postepy Dermatol Alergol., vol. 31 (4):256-261, 2014.

\* cited by examiner

*Primary Examiner* — Allison M Fox
(74) *Attorney, Agent, or Firm* — Norton Rose Fulbright US LLP

(57) ABSTRACT

Described are means, methods, and compositions useful for treatment of multiple sclerosis through the utilization of fibroblasts and/or derivatives thereof to concurrently stimulate regenerative processes while inducing a protolerogenic immune modulatory program. In certain embodiments, fibroblasts are selected for the concurrent properties of immune modulation and regeneration by enrichment for CD73 expressing fibroblasts. In particular embodiments, stimulation of regeneration implies activation of endogenous neural progenitor cells. In some embodiments, stimulation of regeneration implies induction of remyelination. The utilization of fibroblasts as a superior source for immune modulation, prevention of immune mediated pathology, and activation of T regulatory cells is provided within the context of multiple sclerosis.

31 Claims, 8 Drawing Sheets

CONCURRENT ACTIVATION OF REGENERATIVE AND TOLEROGENIC PROCESSES BY FIBROBLAST-BASED COMPOSITIONS FOR THE TREATMENT OF MULTIPLE SCLEROSIS

CROSS-REFERENCE TO RELATED APPLICATIONS

This application claims priority to U.S. Provisional Patent Application Ser. No. 62/855,010, filed May 31, 2019, which is incorporated by reference herein in its entirety.

TECHNICAL FIELD

Embodiments of the disclosure concern at least the fields of cell biology, molecular biology, immunology, and medicine.

BACKGROUND

An unfortunate medical reality is that in some situations, the immune system occasionally malfunctions and turns against the cells of the host thereby provoking an autoimmune response. Autoimmunity typically occurs when antigen receptors on immune cells recognize specific self-antigens on host cells and initiate reactions that result in the destruction of the host cells. In some instances, the autoreactive lymphocytes survive longer and continue to induce apoptosis or otherwise eliminate host cells causing autoimmune diseases. Different mechanisms have been described that prevent T lymphocytes from attacking self. These tolerance mechanisms act both on developing and mature T cells. For example, thymic positive selection skews the T cell repertoire to recognize self-MHC molecules and thus also enriches for auto-reactive T cells (2,3). On the other hand, thymic negative selection, which follows positive selection, eliminates auto-reactive T cells either by clonal deletion (death) or inactivation, (anergy). Whereas clonal deletion deals with high affinity T cells at the CD4+CD8+ $TCR^{high}$ maturation stage, clonal inactivation seems to work at lower affinity interaction possibly by the down-regulation of the TCR and the CD8α-chain. However, these "anergic" T lymphocytes still have the ability to specifically respond to their antigen. It has been suggested that they actually might represent a population of regulatory T cells since they release IL-10 and TGF-β upon stimulation. Thus, it is well-established that thymic (central) tolerance mechanisms do not eliminate all autoreactive T cells. Indeed, T cells reactive with self-antigens, such as myelin basic protein (MBP), insulin and glutamic acid decarboxylase (GAD), can be readily found in the periphery.

In patients with certain genetic abnormalities or predispositions, the tolerogenic processes do not possess full ability to prevent autoreactivity, and when combined with proper stimulation, tolerance to self is broken and pathology ensues. The induction of autoimmunity is associated with various immunological cells interacting and consistently overcoming tolerogenic processes. Both CD4+ helper T cells as well as CD8+ cytotoxic T cells (CTLs) play important roles in the autoantigen immune response. In the well-accepted NOD mouse model of spontaneous diabetes, for example, both CD4+ and CD8+ T cells are crucial for disease development. Directly- and indirectly-primed CD4+ T cells help in the production of autoantibody and provide the signals required for induction of CD8+CTLs, both of which are capable of injuring the cells expressing the autoantigen. Thus, the success of any immunosuppressive strategy directed against an autoimmune response depends on the effective inhibition of both major subsets of T cells.

Existing treatments for autoimmune diseases have had only limited success. For example, it is often possible to correct organ-specific autoimmune disease through metabolic control. Where function is lost and cannot be restored, mechanical substitutes or tissue grafts may be appropriate. While it may be possible to alleviate some of the symptoms using this approach, no effective long-term curative treatment exists for several of the most disabling autoimmune disorders, including multiple sclerosis and insulin-dependent diabetes mellitus (IDDM). While a number of compounds, including insulin, corticosteroids and modified beta interferon can ameliorate some of the symptoms of autoimmune diseases, they can have serious side effects and/or require long-term use. General immunosuppressive drug therapies, such as chronic treatment with cyclosporin A, FK506 and rapamycin have also been unable to provide a cure for these diseases, and their use is accompanied by a host of deleterious side effects. Said effects include nephrotoxicity, increased predisposition to infectious diseases, and enhanced incidence of neoplasia.

A more advanced approach to treatment of autoimmunity is the use of immune modulatory strategies that are antigen-specific. Examples that have been proposed based on the systemic administration of DNA vaccines encoding autoantigens, either alone or in combination with T-helper type 2 (Th2) cytokines such as IL-4 and IL-10. U.S. Patent Publication No. US 2003/0148983 A1, the disclosures of which are expressly incorporated by reference herein. The preliminary data reported by these researchers suggested that DNA vaccines encoding the autoantigen alone could potentially anergize autoreactive T cells, while tolerizing vaccines in combination with IL-4 could help induce Th2 responses, which in numerous autoimmune conditions are known to be inhibitory to pathology, which is classically associated with Th1/Th17 cells. Data from another group of researchers suggested that the presence of IL-4 was critical for protection against disease development induced by the tolerizing vaccine. Thus, the success of this therapeutic strategy likely hinges on the co-administration of Th2-associated cytokines or vectors encoding the same along with the tolerizing vaccine to bias a pro-inflammatory T-helper type 1 (Th1) response to more protective Th2 response. Although this vaccine-based strategy has been somewhat effective in a prophylactic setting, it may prove much more difficult to treat an active autoimmune response already heavily biased towards an inflammatory Th1 response.

Accordingly, novel therapeutic compositions and protocols are sought that can inhibit the function of autoreactive T cells, including Th1-type T cells, in a highly specific fashion. It is an object of the present disclosure to inhibit and/or eliminate autoreactive CD4+ and CD8+T lymphocytes to prevent the development of, as well as the progression of, autoimmune diseases.

Multiple sclerosis (MS) is an autoimmune inflammatory disease of the brain and spinal cord characterized by demyelination and chronic neurodegeneration. Although the incidence of MS is higher in women, it shows clinical improvement during pregnancy, followed by temporary post-partum exacerbation. The autoimmune aspect of the condition is manifested by its pathological activity directed against central nervous system (CNS) antigens. The disease is characterized by inflammation in parts of the CNS, leading to the loss of the myelin sheathing around neuronal axons (demyelination), axonal loss, and the eventual death of neurons, oligodendrocytes and glial cells. There are four major clinical types of MS: 1) relapsing-remitting MS (RR-MS), characterized by clearly defined relapses with full recovery or with sequelae and residual deficit upon recovery; periods between disease relapses characterized by a lack of disease progression; 2) secondary progressive MS (SP-MS), characterized by initial relapsing remitting course followed by progression with or without occasional relapses, minor remissions, and plateaus; 3) primary progressive MS (PP-MS), characterized by disease progression from onset with occasional plateaus and temporary minor improvements allowed; and 4) progressive relapsing MS (PR-MS), characterized by progressive disease onset, with clear acute relapses, with or without full recovery; periods between relapses characterized by continuing progression.

An estimated 2,500,000 people in the world suffer from MS. It is one of the most common diseases of the CNS in young adults. MS is a chronic, progressing, disabling disease, which generally strikes its victims at some point after adolescence, with diagnosis generally made between 20 and 40 years of age, although onset may occur earlier. The disease is not directly hereditary, although genetic susceptibility plays a part in its development. MS is a complex disease with heterogeneous clinical, pathological and immunological phenotype.

Clinically, the illness most often presents as a relapsing-remitting disease and, to a lesser extent, as steady progression of neurological disability. Relapsing-remitting MS (RR-MS) presents in the form of recurrent attacks of focal or multifocal neurologic dysfunction. Attacks may occur, remit, and recur, seemingly randomly over many years. Remission is often incomplete and as one attack follows another, a stepwise downward progression ensues with increasing permanent neurological deficit. The usual course of RR-MS is characterized by repeated relapses associated, for the majority of patients, with the eventual onset of disease progression. The subsequent course of the disease is unpredictable, although most patients with a relapsing-remitting disease will eventually develop secondary progressive disease. In the relapsing-remitting phase, relapses alternate with periods of clinical inactivity and may or may not be marked by sequelae depending on the presence of neurological deficits between episodes. Periods between relapses during the relapsing-remitting phase are clinically stable. On the other hand, patients with progressive MS exhibit a steady increase in deficits, as defined above and either from onset or after a period of episodes, but this designation does not preclude the further occurrence of new relapses.

MS pathology is, in part, reflected by the formation of focal inflammatory demyelinating lesions in the white matter, which are the hallmarks in patients with acute and relapsing disease. In patients with progressive disease, the brain is affected in a more global sense, with diffuse but widespread (mainly axonal) damage in the normal appearing white matter and massive demyelination also in the grey matter, particularly, in the cortex.

BRIEF SUMMARY

The present disclosure is directed to methods for treating multiple sclerosis (MS). Certain embodiments concern methods of correcting or ameliorating one or more abnormalities associated with MS in an individual. The individual may be administered fibroblasts at a concentration and frequency sufficient to correct or ameliorate one or more abnormalities associated with MS. The concentration and frequency may be adjusted based on the response of the individual to the fibroblasts.

In certain embodiments, abnormalities associated with MS include, for example, vision loss, pain, fatigue, impaired coordination, cramping, muscle paralysis, dizziness, vertigo, and numbness. In some embodiments, abnormalities associated with MS include an abnormally high level of interleukin (IL)-17 in an individual, an abnormally low level of IL-10 in an individual, and/or an abnormally low level of proliferation of endogenous stem cells in an individual, including endogenous stem cells in the brain of the individual, such as oligodendrocytes and/or neuronal progenitor cells. The endogenous stem cells may be found in the dentate gyrus and/or subventricular zone. In some embodiments, an abnormally low level of endogenous stem cell proliferation comprises a level of endogenous stem cell proliferation that is 10%, 20%, 30%, 40%, 50%, 60%, 70%, 80%, or 90% of the level of endogenous stem cell proliferation in an age-matched healthy control. The level of proliferation may be assessed by functional MRI In some embodiments, the methods of the disclosure include a step of determining that an individual is in need of ascertaining the level of IL-17 and/or IL-10 in the individual. In some embodiments, the methods of the disclosure include a step of determining the level of IL-17 and/or IL-10 in the individual. An abnormally high level of IL-17 in an individual may be determined by measuring levels of IL-17 in the plasma, peripheral blood, and/or cerebral spinal fluid of the individual. In some embodiments, a measured IL-17 level in an individual that is approximately 10%, 20%, 30%, 40%, 50%, 60%, 70%, 80%, 90%, or 100% higher or more than what is found in an age-matched healthy control is an abnormally high level of IL-17 in the individual. In some embodiments, the levels of IL-17 are assessed in cells, including mononuclear cells, CD4 cells, and/or Th17 cells, from peripheral blood. The levels of IL-17 may be assessed in cells subsequent to stimulation, including, for example, stimulation by IL-6, a mitogen (such as phytohemagglutinin), ligation of a T cell receptor (such as by anti-CD3), and/or ligation of the costimulatory CD28 (including with antibodies to CD28).

An abnormally low level of IL-10 in an individual may be determined by measuring levels of IL-10 in the plasma, peripheral blood, and/or cerebral spinal fluid of the individual. In some embodiments, a measured IL-10 level in an individual that is approximately <10%, 10%, 20%, 30%, 40%, 50%, 60%, 70%, 80%, or 90% of the level that is found in an age-matched healthy control is an abnormally low level of IL-10 in the individual. In some embodiments, the levels of IL-10 are assessed in cells, including mononuclear cells, CD4 cells, and/or Th17 cells, from peripheral blood. The levels of IL-10 may be assessed in cells subsequent to stimulation, including, for example, stimulation by IL-6, a mitogen (such as phytohemagglutinin), ligation of a T cell receptor (such as by anti-CD3), and/or ligation of the costimulatory CD28 (including with antibodies to CD28).

Certain embodiments encompassed herein concern the administration of fibroblasts to an individual. The individual may have MS. The individual may have one or more abnormalities associated with MS, including any abnormality encompassed herein. In some embodiments, an individual is administered an effective amount of a population of fibroblasts. The fibroblasts may be administered at a concentration and frequency sufficient to correct or ameliorate one or more abnormalities associated with MS. In some embodiments, the concentration and/or frequency of administration is adjusted based on the response of the individual to the administration of fibroblasts.

The fibroblasts may be from any source. In some embodiments, the fibroblasts are derived from tissue selected from the group consisting of skin, adipose tissue, bone marrow, umbilical cord, Wharton's Jelly, Omentum, peripheral blood, mobilized peripheral blood, and a combination thereof. In some embodiments, mobilization of peripheral blood is performed by administration of agents to an individual selected from the group consisting of G-CSF, GM-CSF, flt-3 ligand, mozibil, hyperbaric oxygen, ozone therapy, and a combination thereof. The fibroblasts may express certain markers, including markers selected from the group consisting of extracellular vimentin, Cyclin D2, Snail, E-cadherin, SOX-2, CD105, CD90, CD29, CD73, Wt1, SSEA3, and a combination thereof. The fibroblasts may be autologous or allogeneic or xenogenic with respect to the individual.

In some embodiments, the fibroblasts are treated with one or more compositions capable of enhancing the fibroblasts' ability to suppress Th3 production of TGF-beta. In some embodiments, the composition capable of enhancing the fibroblasts' ability to suppress Th3 production of TGF-beta comprises oxytocin. In some embodiments, fibroblasts are contacted with one or more compositions capable of enhancing the fibroblasts' ability to suppress Th3 production of TGF-beta for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes. In some embodiments, fibroblasts are contacted with one or more compositions capable of enhancing the fibroblasts' ability to suppress Th3 production of TGF-beta for 1, 2, 3, 4, 5, 6, 7, 8, 9, 10, 11, 12, 13, 14, 15, 16, 17, 18, 19, 20, 21, 22, 23, 24, 48, or 72 hours. In some embodiments, fibroblasts are contacted with one or more compositions capable of enhancing the fibroblasts' ability to suppress Th3 production of TGF-beta for 1, 2, 3, 4, 5, 6, or 6 days. In some embodiments, fibroblasts are contacted with one or more compositions capable of enhancing the fibroblasts' ability to suppress Th3 production of TGF-beta for 1, 2, 3, or 4 weeks. In some embodiments, fibroblasts are contacted with one or more compositions capable of enhancing the fibroblasts' ability to suppress Th3 production of TGF-beta for a period between 1 minute to 4 weeks, or between 2 hours to 1 week, or between 24 hours to 72 hours. In certain embodiments, the fibroblasts are contacted with oxytocin at a concentration between 10 nM to 10 μM, or between 100 nm to 1 μM. The fibroblasts may be assessed for the ability to suppress the Th3 production of TGF-beta subsequent to cell to cell contact between the fibroblasts and Th3 cells.

In some embodiments, the fibroblasts are unmodified. In certain embodiments, the fibroblasts are exposed to hypoxic conditions prior to administration. Hypoxic conditions may comprise conditions with an oxygen level lower than 10%, 9%, 8%, 7%, 6%, 5%, 4%, 3%, 2%, 1%, 0.75%, or 0.5%.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing, in which.

DETAILED DESCRIPTION

I. Definitions

Figure 1:
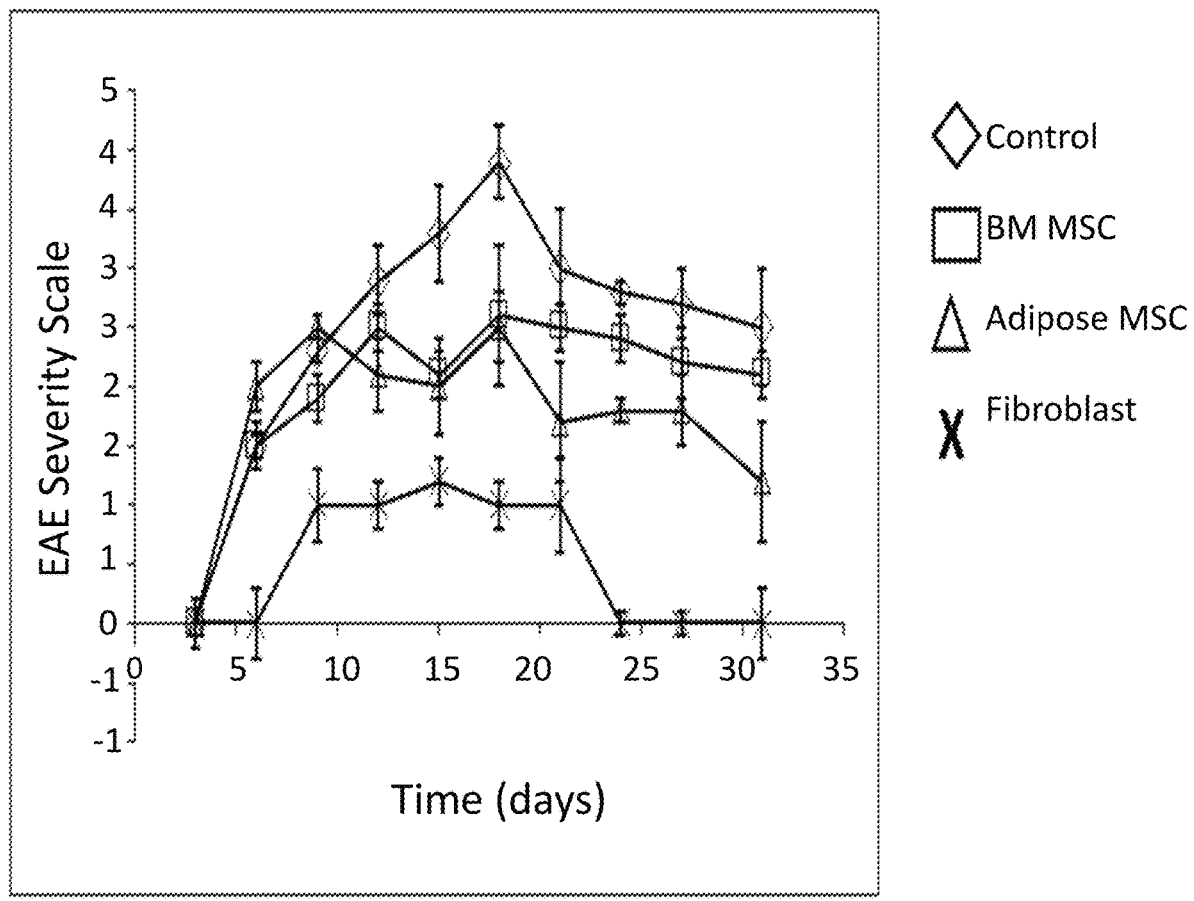
FIG. 1 shows clinical manifestations of experimental autoimmune encephalomyelitis EAE in rats that were administered with a vehicle control, mesenchymal stem cells (MSCs) from bone marrow (BM-MSC) or adipose (Adipose MSC), or fibroblasts.

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

As used herein, the term "therapeutically effective amount" is synonymous with "effective amount", "therapeutically effective dose", and/or "effective dose" and refers to the amount of compound that will elicit the biological, cosmetic or clinical response being sought by the practitioner in an individual in need thereof. As one example, an effective amount is the amount sufficient to reduce immunogenicity of a group of cells. The appropriate effective amount to be administered for a particular application of the disclosed methods can be determined by those skilled in the art, using the guidance provided herein. For example, an effective amount can be extrapolated from in vitro and in vivo assays as described in the present specification. One skilled in the art will recognize that the condition of the individual can be monitored throughout the course of therapy and that the effective amount of a compound or composition disclosed herein that is administered can be adjusted accordingly.

"Allogeneic," as used herein, refers to cells of the same species that differ genetically from cells of a host.

"Autologous," as used herein, refers to cells derived from the same subject. The term "engraft" as used herein refers to the process of stem cell incorporation into a tissue of interest in vivo through contact with existing cells of the tissue.

"Xenogeneic," as used herein, refers to cells derived from, originating in, or being a member of another species.

"Approximately" or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "expresses", when referring to a gene, nucleic acid, protein, cell marker, or the like, means that expression of the gene, nucleic acid, protein, cell marker can be detected by standard methods. In the case of cell surface markers, expression can be measured by, e.g., flow cytometry, using a cut-off values as obtained from negative controls (i.e., cells known to lack the antigen of interest) or by isotype controls (i.e., measuring nonspecific binding of the antibody to the cell). For gene expression, a gene is said to be expressed if the presence of its mRNA can be detected using standard methods. For example, a gene can be said to be expressed by a cell if the mRNA transcribed from the gene can be detected on a standard agarose gel following standard PCR protocols.

The term "fibroblast" are typically from one or more various tissues selected for specific properties associated with regenerative activity. Tissues useful for the practice of the disclosure are generally tissues associated with regenerative activity. Said tissues include, as non-limiting examples, placenta, endometrial cells, Wharton's jelly, bone marrow, and adipose tissue. In a certain embodiments, cells are selected for expression of the markers CD117, CD105, and expression of the rhodamine 123 efflux activity. In some embodiments of the disclosure, fibroblasts are selected for expression of markers selected from a group comprising of additional markers Oct-4, CD-34, KLF-4, Nanog, Sox-2, Rex-1, GDF-3, Stella, and possesses enhanced expression of GDF-11. Selection of fibroblasts for expression of said markers may be performed by initial expression of proteins found on the membrane of the cells, which result in possessing other markers mentioned.

The term "individual" may be used interchangeably with "subject" and generally refers to an individual in need of a therapy. The individual can be a mammal, such as a human, dog, cat, horse, pig or rodent. The individual can be a patient, e.g., have or be suspected of having or at risk for having a disease or medical condition related to bone. For individuals having or suspected of having a medical condition directly or indirectly associated with bone, the medical condition may be of one or more types. The individual may have a disease or be suspected of having the disease. The individual may be asymptomatic. The individual may be of any gender. The individual may be of a certain age, such as at least 20, 25, 30, 35, 40, 45, 50, 55, 60, 65, 70, 75, 80, 85, 90, 95, or 100 or more.

The term "passaging" refers to the process of transferring a portion of cells from one culture vessel into a new culture vessel.

The term "cryopreserve" refers to preserving cells for long term storage in a cryoprotectant at low temperature.

The term "master cell bank" refers to a collection of cryopreserved cells. Such a cell bank may comprise stem cells, non-stem cells, and/or a mixture of stem cells and non-stem cells.

II. Fibroblast Characterization and Preparation

In certain embodiments, the disclosure provides methods of increasing T regulatory cell activity in a patient suffering from multiple sclerosis through administration of fibroblasts and/or fibroblasts that have been modified to enhance immune modulatory activity. It is known that T regulatory cells play a role in the prevention and/or suppression of autoimmunity in general, and especially in multiple sclerosis. The role of Treg cells is universally associated with tolerance in conditions of natural tolerance such as in pregnancy (4,5), transplantation tolerance (6-10), and ocular tolerance (11-20). The functional relevance of Treg cells to preservation and/or initiation of tolerance is observed in conditions where administration of Tregs prevents pathology, such as in spontaneous abortion (21).

The disclosure provides that administration of fibroblasts, in part through induction of T regulatory cells, enhances neurogenic processes, which are manifested in part, by enhancement of proliferation of endogenous neural stem cells, including cells in the dendate gyrus and subventricular zone. The disclosure provides that, under conditions of certain embodiments, the administration of fibroblasts inhibits IL-17 and/or augments IL-10. Furthermore, the disclosure provides that administration of fibroblast induces biological processes associated with remyelination and reduction of multiple sclerosis pathology. In some embodiments, the invention provides that administration of fibroblast results in superior therapeutic response to autoimmunity as compared to other stem cell types such as mesenchymal stem cells.

The fibroblasts utilized in the disclosure are generated, in particular embodiments, by outgrowth from a biopsy of the recipient's own skin (in the case of autologous preparations), or skin of healthy donors (for allogeneic preparations). In some embodiments, fibroblasts are used from young donors. In certain embodiments, fibroblasts are transfected with genes to allow for enhanced growth and overcoming of the Hayflick limit subsequent to derivation of cells expansion in culture using standard cell culture techniques. Skin tissue (dermis and epidermis layers) may be biopsied from a subject's post-auricular area. In some embodiments, the starting material is composed of three 3-mm punch skin biopsies collected using standard aseptic practices. The biopsies are collected by the treating physician, placed into a vial containing sterile phosphate buffered saline (PBS). The biopsies are shipped in a 2-8° C. refrigerated shipper back to the manufacturing facility. In some embodiments, after arrival at the manufacturing facility, the biopsy is inspected and, upon acceptance, transferred directly to the manufacturing area.

Upon initiation of the process, the biopsy tissue is then washed prior to enzymatic digestion. After washing, a Liberase Digestive Enzyme Solution is added without mincing, and the biopsy tissue is incubated at 37.0±2° C. for one hour. Time of biopsy tissue digestion is a critical process parameter that can affect the viability and growth rate of cells in culture. Liberase is a collagenase/neutral protease enzyme cocktail obtained formulated from Lonza Walkersville, Inc. (Walkersville, Md.) and unformulated from Roche Diagnostics Corp. (Indianapolis, Ind.). Alternatively, other commercially available collagenases may be used, such as Serva Collagenase NB6 (Heidelberg, Germany). After digestion, Initiation Growth Media (IMDM, GA, 10% Fetal Bovine Serum (FBS)) is added to neutralize the enzyme, cells are pelleted by centrifugation and resuspended in 5.0 mL Initiation Growth Media. Alternatively, centrifugation is not performed, with full inactivation of the enzyme occurring by the addition of Initiation Growth Media only. Initiation Growth Media is added prior to seeding of the cell suspension into a T-175 cell culture flask for initiation of cell growth and expansion. A T-75, T-150, T-185 or T-225 flask can be used in place of the T-75 flask.

Cells are incubated at 37±2.0° C. with 5.0±1.0% $CO_2$ and fed with fresh Complete Growth Media every three to five days. All feeds in the process are performed by removing half of the Complete Growth Media and replacing the same volume with fresh media. Alternatively, full feeds can be performed. Cells should not remain in the T-175 flask greater than 30 days prior to passaging. Confluence is monitored throughout the process to ensure adequate seeding densities during culture splitting. When cell confluence is greater than or equal to 40% in the T-175 flask, they are passaged by removing the spent media, washing the cells, and treating with Trypsin-EDTA to release adherent cells in the flask into the solution. Cells are then trypsinized and seeded into a T-500 flask for continued cell expansion. Alternately, one or two T-300 flasks, One Layer Cell Stack (1 CS), One Layer Cell Factory (1 CF) or a Two Layer Cell Stack (2 CS) can be used in place of the T-500 Flask.

Morphology is evaluated at each passage and prior to harvest to monitor the culture purity throughout the culture purity throughout the process. Morphology is evaluated by comparing the observed sample with visual standards for morphology examination of cell cultures. The cells display typical fibroblast morphologies when growing in cultured monolayers. Cells may display either an elongated, fusiform or spindle appearance with slender extensions, or appear as larger, flattened stellate cells which may have cytoplasmic leading edges. A mixture of these morphologies may also be observed. Fibroblasts in less confluent areas can be similarly shaped, but randomly oriented. The presence of keratinocytes in cell cultures is also evaluated. Keratinocytes appear round and irregularly shaped and, at higher confluence, they appear organized in a cobblestone formation. At lower confluence, keratinocytes are observable in small colonies. Cells are incubated at 37±2.0° C. with 5.0±1.0% $CO_2$ and passaged every three to five days in the T-500 flask and every five to seven days in the ten layer cell stack (10CS). Cells should not remain in the T-500 flask for more than 10 days prior to passaging. Quality Control (QC) release testing for safety of the Bulk Drug Substance includes sterility and endotoxin testing. When cell confluence in the T-500 flask is ~95%, cells are passaged to a 10 CS culture vessel. Alternately, two Five Layer Cell Stacks (5 CS) or a 10 Layer Cell Factory (10 CF) can be used in place of the 10 CS. Passage to the 10 CS is performed by removing the spent media, washing the cells, and treating with Trypsin-EDTA to release adherent cells in the flask into the solution. Cells are then transferred to the 10 CS. Additional Complete Growth Media is added to neutralize the trypsin and the cells from the T-500 flask are pipetted into a 2 L bottle containing fresh Complete Growth Media. The contents of the 2 L bottle are transferred into the 10 CS and seeded across all layers. Cells are then incubated at 37±2.0° C. with 5.0±1.0% $CO_2$ and fed with fresh Complete Growth Media every five to seven days. Cells should not remain in the 10CS for more than 20 days prior to passaging.

In some embodiments, the passaged dermal fibroblasts are rendered substantially free of immunogenic proteins present in the culture medium by incubating the expanded fibroblasts for a period of time in protein free medium, Primary Harvest When cell confluence in the 10 CS is 95% or more, cells are harvested. Harvesting is performed by removing the spent media, washing the cells, treating with Trypsin-EDTA to release adherent cells into the solution, and adding additional Complete Growth Media to neutralize the trypsin. Cells are collected by centrifugation, resuspended, and in-process QC testing performed to determine total viable cell count and cell viability.

In some embodiments, when large numbers of cells are required after receiving cell count results from the primary 10 CS harvest, an additional passage into multiple cell stacks (up to four 10 CS) is performed. For additional passaging, cells from the primary harvest are added to a 2 L media bottle containing fresh Complete Growth Media. Resuspended cells are added to multiple cell stacks and incubated at 37±2.0° C. with 5.0±1.0% $CO_2$ The cell stacks are fed and harvested as described above, except cell confluence must be 80% or higher prior to cell harvest. The harvest procedure is the same as described for the primary harvest above. A mycoplasma sample from cells and spent media is collected, and cell count and viability performed as described for the primary harvest above. The method decreases or eliminates immunogenic proteins be avoiding their introduction from animal-sourced reagents. To reduce process residuals, cells are cryopreserved in protein-free freeze media, then thawed and washed prior to prepping the final injection to further reduce remaining residuals. If additional Drug Substance is needed after the harvest and cryopreservation of cells from additional passaging is complete, aliquots of frozen Drug Substance—Cryovial are thawed and used to seed 5 CS or 10 CS culture vessels. Alternatively, a four layer cell factory (4 CF), two 4 CF, or two 5 CS can be used in place of a 5 CS or 10 CS. A frozen cryovial(s) of cells is thawed, washed, added to a 2 L media bottle containing fresh Complete Growth Media and cultured, harvested and cryopreserved as described above. The cell suspension is added Cell confluence must be 80% or more prior to cell harvest.

At the completion of culture expansion, the cells are harvested and washed, then formulated to contain $1.0$-$2.7 \times 10^7$ cells/mL, with a target of $2.2 \times 10^7$ cells/mL. Alternatively, the target can be adjusted within the formulation range to accommodate different indication doses. The drug substance consists of a population of viable, autologous human fibroblast cells suspended in a cryopreservation medium consisting of Iscove's Modified Dulbecco's Medium (IMDM) and Profreeze-CDM™ (Lonza, Walkerville, Md.) plus 7.5% dimethyl sulfoxide (DMSO). Alternatively, a lower DMSO concentration may be used in place of 7.5% or CryoStor™ CS5 or CryoStor™ CS10 (BioLife Solutions, Bothell, Wash.) may be used in place of IMDM/Profreeze/DMSO. In addition to cell count and viability, purity/identity of the Drug Substance is performed and must confirm the suspension contains 98% or more fibroblasts. The usual cell contaminants include keratinocytes. The purity/identify assay employs fluorescent-tagged antibodies against CD90 and CD104 (cell surface markers for fibroblast and keratinocyte cells, respectively) to quantify the percent purity of a fibroblast cell population. CD90 (Thy-1) is a 35 kDa cell-surface glycoprotein. Antibodies against CD90 protein have been shown to exhibit high specificity to human fibroblast cells. CD104, integrin β4 chain, is a 205 kDa transmembrane glycoprotein which associates with integrin α6 chain (CD49f) to form the α6/β4 complex. This complex has been shown to act as a molecular marker for keratinocyte cells (Adams and Watt 1991).

Antibodies to CD 104 protein bind to 100% of human keratinocyte cells. Cell count and viability is determined by incubating the samples with Viacount Dye Reagent and analyzing samples using the Guava PCA system. The reagent is composed of two dyes, a membrane-permeable dye which stains all nucleated cells, and a membrane-impermeable dye which stains only damaged or dying cells. The use of this dye combination enables the Guava PCA system to estimate the total number of cells present in the sample, and to determine which cells are viable, apoptotic, or dead. The method was custom developed specifically for use in determining purity/identity of autologous cultured fibroblasts. Alternatively, cells can be passaged from either the T-175 flask (or alternatives) or the T-500 flask (or alternatives) into a spinner flask containing microcarriers as the cell growth surface. Microcarriers are small bead-like structures that are used as a growth surface for anchorage dependent cells in suspension culture. They are designed to produce large cell yields in small volumes. In this apparatus, a volume of Complete Growth Media ranging from 50 mL-300 mL is added to a 500 mL, IL or 2 L sterile disposable spinner flask. Sterile microcarriers are added to the spinner flask. The culture is allowed to remain static or is placed on a stir plate at a low RPM (15-30 RRM) for a short period of time (1-24 hours) in a $37 \pm 2.0°$ C. with $5.0 \pm 1.0\%$ $CO_2$ incubator to allow for adherence of cells to the carriers. After the attachment period, the speed of the spin plate is increased (30-120 RPM). Cells are fed with fresh Complete Growth Media every one to five days, or when media appears spent by color change. Cells are collected at regular intervals by sampling the microcarriers, isolating the cells and performing cell count and viability analysis. The concentration of cells per carrier is used to determine when to scale-up the culture. When enough cells are produced, cells are washed with PBS and harvested from the microcarriers using trypsin-EDTA and seeded back into the spinner flask in a larger amount of microcarriers and higher volume of Complete Growth Media (300 mL-2 L). Alternatively, additional microcarriers and Complete Growth Media can be added directly to the spinner flask containing the existing microcarrier culture, allowing for direct bead-to-bead transfer of cells without the use of trypsinization and reseeding. Alternatively, if enough cells are produced from the initial T-175 or T-500 flask, the cells can be directly seeded into the scale-up amount of microcarriers. After the attachment period, the speed of the spin plate is increased (30-120 RPM). Cells are fed with fresh Complete Growth Media every one to five days, or when media appears spent by color change. When the concentration reaches the desired cell count for the intended indication, the cells are washed with PBS and harvested using trypsin-EDTA. Microcarriers used within the disposable spinner flask may be made from poly blend such as BioNOC II® (Cesco Bioengineering, distributed by Bellco Biotechnology, Vineland, N.J.) and FibraCel® (New Brunswick Scientific, Edison, N.J.), gelatin, such as Cultispher-G (Percell Biolytica, Astrop, Sweden), cellulose, such as Cytopore™ (GE Healthcare, Piscataway, N.J.) or coated/uncoated polystyrene, such as 2D MicroHex™ (Nunc, Weisbaden, Germany), Cytodex® (GE Healthcare, Piscataway, N.J.) or Hy-Q Sphere™ (Thermo Scientific Hyclone, Logan, Utah).

In certain embodiments, the isolation procedure also utilizes an enzymatic digestion process. Many enzymes are known in the art to be useful for the isolation of individual cells from complex tissue matrices to facilitate growth in culture. As discussed above, a broad range of digestive enzymes for use in cell isolation from tissue is available to the skilled artisan. Ranging from weakly digestive (e.g. deoxyribonucleases and the neutral protease, dispase) to strongly digestive (e.g. papain and trypsin), such enzymes are available commercially. A nonexhaustive list of enzymes compatible herewith includes mucolytic enzyme activities, metalloproteases, neutral proteases, serine proteases (such as trypsin, chymotrypsin, or elastase), and deoxyribonucleases. Certain embodiments concern enzyme activities selected from metalloproteases, neutral proteases and mucolytic activities. For example, collagenases are known to be useful for isolating various cells from tissues. Deoxyribonucleases can digest single-stranded DNA and can minimize cell-clumping during isolation. Enzymes can be used alone or in combination. Serine protease may be used in a sequence following the use of other enzymes as they may degrade the other enzymes being used. The temperature and time of contact with serine proteases must be monitored. Serine proteases may be inhibited with alpha 2 microglobulin in serum and therefore the medium used for digestion is optionally serum-free. EDTA and DNase are commonly used and may improve yields or efficiencies. Certain methods involve enzymatic treatment with for example collagenase and dispase, or collagenase, dispase, and hyaluronidase, and such methods are provided wherein in certain embodiments, a mixture of collagenase and the neutral protease dispase are used in the dissociating step. Certain methods employ digestion in the presence of at least one collagenase from *Clostridium histolyticum*, and either of the protease activities, dispase and thermolysin. Certain methods employ digestion with both collagenase and dispase enzyme activities. Certain methods include digestion with a hyaluronidase activity in addition to collagenase and dispase activities. The skilled artisan will appreciate that many such enzyme treatments are known in the art for isolating cells from various tissue sources. For example, the LIBERASE BLENDZYME (Roche) series of enzyme combinations of collagenase and neutral protease are very useful and may be used in the instant methods. Other sources of enzymes are known, and the skilled artisan may also obtain such enzymes directly from their natural sources. The skilled artisan is also well-equipped to assess new, or additional enzymes or enzyme combinations for their utility in isolating the cells of the invention. Enzyme treatments may be approximately 0.5, 1, 1.5, or 2 hours long or longer. In certain embodiments, the tissue is incubated at 37° C. during the enzyme treatment of the dissociation step. Diluting the digest may also improve yields of cells as cells may be trapped within a viscous digest.

While certain embodiments encompass enzyme activities, it is not required for isolation methods as provided herein. Methods based on mechanical separation alone may be successful in isolating the instant cells from the umbilicus as discussed above.

The cells can be resuspended after the tissue is dissociated into any culture medium as discussed herein above. Cells may be resuspended following a centrifugation step to separate out the cells from tissue or other debris. Resuspension may involve mechanical methods of resuspending, or simply the addition of culture medium to the cells.

Providing the growth conditions allows for a wide range of options as to culture medium, supplements, atmospheric conditions, and relative humidity for the cells. In certain embodiments, the culture temperature is 37° C., however the temperature may range from about 35° C. to 39° C. depending on the other culture conditions and desired use of the cells or culture.

Certain methods encompassed herein provide cells which require no exogenous growth factors, except as are available in the supplemental serum provided with the Growth Medium. Also provided herein are methods of deriving umbilical cells capable of expansion in the absence of particular growth factors. The methods are similar to the method above, however they require that the particular growth factors (for which the cells have no requirement) be absent in the culture medium in which the cells are ultimately resuspended and grown in. In this sense, the method is selective for those cells capable of division in the absence of the particular growth factors. In some embodiments, cells encompassed herein are capable of growth and expansion in chemically-defined growth media with no serum added. In such cases, the cells may require certain growth factors, which can be added to the medium to support and sustain the cells. Certain factors to be added for growth on serum-free media include one or more of FGF, EGF, IGF, and PDGF. In particular embodiments, two, three or all four of the factors are add to serum free or chemically defined media. In other embodiments, LIF is added to serum-free medium to support or improve growth of the cells.

Also provided are methods wherein the cells can expand in the presence of from about 5% to about 20% oxygen in their atmosphere. Methods to obtain cells that require L-valine require that cells be cultured in the presence of L-valine. After a cell is obtained, its need for L-valine can be tested and confirmed by growing on D-valine containing medium that lacks the L-isomer.

Methods are provided wherein the cells can undergo at least 25, 30, 35, or 40 doublings prior to reaching a senescent state. Methods for deriving cells capable of doubling to reach $10^{14}$ cells or more are provided. Certain methods derive cells that can double sufficiently to produce at least about $10^{14}$, $10^{15}$, $10^{16}$, or $10^{17}$ or more cells when seeded at from about $10^3$ to about $10^6$ cells/cm$^2$ in culture. These cell numbers may be produced within 80, 70, or 60 days or less. In some embodiments, cord tissue mesenchymal stem cells are isolated and expanded, and possess one or more markers selected from a group comprising of CD10, CD13, CD44, CD73, CD90, CD141, PDGFr-alpha, or HLA-A,B,C. In addition, the cells do not produce one or more of CD31, CD34, CD45, CD117, CD141, or HLA-DR, DP, DQ.

In another embodiment, cells can be processed on poly blend 2D microcarriers such as BioNOC II® and FibraCel® using an automatic bellow system, such as FibraStage™ (New Brunswick Scientific, Edison, N.J.) or BelloCell® (Cesco Bioengineering, distributed by Bellco Biotechnology, Vineland, N.J.) in place of the spinner flask apparatus. Cells from the T-175 (or alternatives) or T-500 flask (or alternatives) are passaged into a bellow bottle containing microcarriers with the appropriate amount of Complete Growth Media, and placed into the system. The system pumps media over the microcarriers to feed cells, and draws away media to allow for oxygenation in a repeating fixed cycle. Cells are monitored, fed, washed and harvested in the same sequence as described above. Alternatively, cells can be processed using automated systems. After digestion of the biopsy tissue or after the first passage is complete (T-175 flask or alternative), cells may be seeded into an automated device. One method is an Automated Cellular Expansion (ACE) system, which is a series of commercially available or custom fabricated components linked together to form a cell growth platform in which cells can be expanded without human intervention. Cells are expanded in a cell tower, consisting of a stack of disks capable of supporting anchorage-dependent cell attachment. The system automatically circulates media and performs trypsinization for harvest upon completion of the cell expansion stage.

Alternatively, the ACE system can be a scaled down, single lot unit version comprised of a disposable component that consists of cell growth surface, delivery tubing, media and reagents, and a permanent base that houses mechanics and computer processing capabilities for heating/cooling, media transfer and execution of the automated programming cycle. Upon receipt, each sterile irradiated ACE disposable unit will be unwrapped from its packaging and loaded with media and reagents by hanging pre-filled bags and connecting the bags to the existing tubing via aseptic connectors. The process continues as follows: a) Inside a biological safety cabinet (BSC), a suspension of cells from a biopsy that has been enzymatically digested is introduced into the "pre-growth chamber" (small unit on top of the cell tower), which is already filled with Initiation Growth Media containing antibiotics. From the BSC, the disposable would be transferred to the permanent ACE unit already in place. After approximately three days, the cells within the pre-growth chamber are trypsinized and introduced into the cell tower itself, which is pre-filled with Complete Growth Media. Here, the "bubbling action" caused by $CO_2$ injection force the media to circulate at such a rate that the cells spiral downward and settle on the surface of the discs in an evenly distributed manner. For approximately seven days, the cells are allowed to multiply. At this time, confluence will be checked (method unknown at time of writing) to verify that culture is growing. Also at this time, the Complete Growth Media will be replaced with fresh Complete Growth Media. CGM will be replaced every seven days for three to four weeks. At the end of the culture period, the confluence is checked once more to verify that there is sufficient growth to possibly yield the desired quantity of cells for the intended treatment; d) If the culture is sufficiently confluent, it is harvested. The spent media (supernatant) is drained from the vessel. PBS will then is pumped into the vessel (to wash the media, FBS from the cells) and drained almost immediately. Trypsin-EDTA is pumped into the vessel to detach the cells from the growth surface. The trypsin/cell mixture is drained from the vessel and enter the spin separato. Cryopreservative is pumped into the vessel to rinse any residual cells from the surface of the discs, and be sent to the spin separator as well. The spin separator collects the cells and then evenly resuspend the cells in the shipping/injection medium. From the spin separator, the cells will be sent through an inline automated cell counting device or a sample collected for cell count and viability testing via laboratory analyses. Once a specific number of cells has been counted and the proper cell concentration has been reached, the harvested cells are delivered to a collection vial that can be removed to aliquot the samples for cryogenic freezing.

In another embodiment, automated robotic systems may be used to perform cell feeding, passaging, and harvesting for the entire length or a portion of the process. Cells can be introduced into the robotic device directly after digest and seed into the T-175 flask (or alternative). The device may have the capacity to incubate cells, perform cell count and viability analysis and perform feeds and transfers to larger culture vessels. The system may also have a computerized cataloging function to track individual lots. Existing technologies or customized systems may be used for the robotic option.

In some embodiments, fibroblasts are preactivated by contact with a growth factor containing mixture, said mixture, or composition may comprise growth factors selected from the group consisting of transforming growth factors (TGF), fibroblast growth factors (FGF), platelet-derived growth factors (PDGF), epidermal growth factors (EGF), vascular endothelial growth factors (VEGF), insulin-like growth factors (IGF), platelet-derived endothelial growth factors (PDEGF), platelet-derived angiogenesis factors (PDAF), platelet factors 4 (PF-4), hepatocyte growth factors (HGF) and mixtures thereof. In some embodiments, the growth factors are transforming growth factors (TGF), platelet-derived growth factors (PDGF) fibroblast growth factors (FGF) or mixtures thereof. In particular embodiments, the growth factors are selected from the group consisting of transforming growth factors β (TGF-β), platelet-derived growth factors BB (PDGF-BB), basic fibroblast growth factors (bFGF) and mixtures thereof. In another embodiment of the disclosure, said growth factor containing compositions are injected simultaneously with, or subsequent to, injection of fibroblasts. Said fibroblasts may be autologous, allogeneic, or xenogeneic.

In some embodiments a platelet plasma composition is administered together with fibroblasts or subsequent to administration of fibroblasts. The platelet plasma may comprise, composition, consist essentially of, or consist of platelets and plasma, and may be derived from bone marrow or peripheral blood. The present disclosure may use platelet plasma compositions from either or both of these sources, and either platelet plasma composition may be used to regenerate either a nucleus or annulus in need thereof. Further, the platelet plasma composition may be used with or without concentrated bone marrow (BMAC). By way of example, when inserted into the annulus, 0.05-2.0 cc of platelet plasma composition may be used, and when inserted into the nucleus, 0.05-3.0 cc of the platelet plasma composition may be used. Platelets are non-nucleated blood cells that as noted above are found in bone marrow and peripheral blood. They have several important functions such as controlling bleeding and tissue healing. As persons of ordinary skill in the art are aware, the ability to promote tissue healing is due to the many growth factors that they produce including platelet-derived growth factor (PDGF), transforming growth factor beta (TGF-beta), fibroblast growth factor (FGF), insulin-like growth factor-1 (IGF-1), connective tissue growth factor (CTGF) and vascular endothelial growth factor (VEGF). Many of these platelet proteins and molecules are cytokines and are important for cell signaling and immunomodulation.

In various embodiments of the present disclosure, the platelet plasma composition may be obtained by sequestering platelets from whole blood or bone marrow through centrifugation into three strata: (1) platelet rich plasma; (2) platelet poor plasma; and (3) fibrinogen. When using platelets from one of the strata, e.g., the platelet rich plasma (PRP) from blood, one may use the platelets whole or their contents may be extracted and concentrated into a platelet lysate through a cell membrane lysis procedure using thrombin and/or calcium chloride. When choosing whether to use the platelets whole or as a lysate, one may consider the rate at which one desires regeneration and/or tissue healing (which may include the formation of scar tissue without regeneration or healing of a herniated or torn disc). In some embodiments the lysate will act more rapidly than the PRP (or platelet poor plasma from bone marrow).

Notably, platelet poor plasma that is derived from bone marrow has a greater platelet concentration than platelet rich plasma from blood, also known as platelet poor/rich plasma, ("PP/RP" or "PPP"). PP/RP or PPP may be used to refer to platelet poor plasma derived from bone marrow, and in some embodiments, PP/RP is used or PRP is used as part of the composition for disc regeneration. By convention, the abbreviation PRP refers only to compositions derived from peripheral blood and PPP (or PP/RP) refers to compositions derived from bone marrow. In various embodiments, the platelet plasma composition, which may or may not be in the form of a lysate, may serve one or more of the following functions: (1) to release/provide growth factors and cytokines for tissue regeneration; (2) to reduce inflammation; (3) to attract/mobilize cell signaling; and (4) to stimulate stem cell activation. Additionally, by combining platelet therapy with stem cells, there can be synergy with respect to reducing back pain.

In some embodiments in which the lysate is used, the cytokines are concentrated in order to optimize their functional capacity. Concentration may be accomplished in two steps. First, blood may be obtained and concentrated to a volume that is 5-15% of what it was before concentration. Devices that may be used include but are not limited to a hemofilter or a hemoconcentrator. For example, 60 cc of blood may be concentrated down to 6 cc. Next, the concentrated blood may be filtered to remove water. This filtering step may reduce the volume further to 33%-67% (e.g., approximately 50%) of what it was prior to filtration. Thus, by way of example for a concentration product of 6 cc, one may filter out water so that one obtains a product of approximately 3 cc. When the platelet rich plasma, platelet poor plasma and fibrinogen are obtained from blood, they may for example be obtained by drawing 20-500 cc of peripheral blood, 40-250 cc of peripheral blood or 60-100 cc of peripheral blood. In one specific embodiment fibroblasts are treated, or administered together with activated PRP. The method of generation of said activated PRP may be used according to U.S. Pat. No. 9,011,929, which describes essentially: separating the PRP from whole blood, wherein the separating step further comprises the steps of: collecting 10 ml of the whole blood from an animal or patient into a vacuum test tube containing 3.2% sodium citrate, and primarily centrifuging the collected whole blood at 1,750-1,900 g for 3 to 5 minutes; collecting a supernatant liquid comprising a plasma layer with a buffy coat obtained from said centrifugation; transferring the collected supernatant liquid to a new vacuum test tube by a blunt needle, and secondarily centrifuging the collected supernatant liquid at 4,500-5,000 g for 4 to 6 minutes; and collecting the PRP concentrated in a bottom layer by another blunt needle; mixing 1 mL of the PRP collected from the separating step with a calcium chloride solution with a concentration of 0.30-0.55 mg/mL by a three-way connector; and mixing a mixture of the PRP and the calcium chloride solution with type I collagen, wherein the mixing step of mixing the mixture of the PRP and the calcium chloride solution with the type I collagen further comprises the steps of: leaving the type I collagen at a room temperature for 15 to 30 minutes before mixing; and mixing the mixture of the PRP and the calcium chloride solution with the type I collagen with a concentration of 20-50 mg/mL, in an opaque phase, four times by another three-way connector. In some embodiments administration of fibroblasts is performed together with biocompatible polymers and growth factors or PRP, or Platelet Gel.

In some embodiments allogeneic fibroblasts are obtained from a screened donor(s) using similar methods as described above. In this embodiment, a screened donor provides tissue for expansion of fibroblasts and creation of a master cell bank (MCB). After appropriate tests are conducted on the MCB, cells expanded from the master bank are used to create a working cell bank (WCB), which is in turn expanded for manufacture of conditioned media for use in the formulation of the product. The manufacturing process is similar to the autologous process, has the same applications and all final formulations are within the same concentration ranges. Somatic cells transfected with retroviral vectors that express OCT4, SOX2, KLF4 and cMYC to generate induced pluripotent stem cells ("iPSCs") express the same pluripotency markers as control H9 ESCs. Reprogrammed cells possess a normal karyotype, differentiate into beating cardiomyocytes in vitro and differentiate into representatives of all three germ layers in vivo. A subpopulation of human dermal fibroblasts that express the pluripotency marker stage specific embryonic antigen 3 (SSEA3) demonstrates enhanced iPSC generation efficiency as described by Bryne, et al., PLoS One, 4(9):e7118 (2009). SSEA3-positive and SSEA3-negative populations were transduced with the same retroviral vectors, under identical experimental conditions, and seeded onto inactivated mouse embryonic fibroblasts (MEFs). After three weeks of culture under standard hESC conditions, plates were examined in a double-blind analysis by three independent hESC biologists for iPSC colony formation. Colonies with iPSC morphology were picked and expanded. All three biological replicates with the transduced SSEA3-negative cells formed many large background colonies (10-27 per replicate) but no iPSC colonies emerged; in contrast, all three biological replicates with the transduced SSEA3-positive cells resulted in the formation of iPSC colonies (4-5 per replicate) but very few large background colonies (0-1 per replicate). Further characterization of the cell lines derived from the iPSC-like colonies showed that they possessed hESC-like morphology, growing as flat colonies with large nucleo-cytoplasmic ratios, defined borders and prominent nucleoli. When five lines were further expanded and characterized, all demonstrated expression of key pluripotency markers expressed by hESCs, which included alkaline phosphatase, Nanog, SSEA3, SSEA4, TRA160 and TRA181. The SSEA3-selected iPSCs also demonstrated a normal male karyotype (46, XY), the ability to differentiate into functional beating cardiomyocytes in vitro and differentiate into representatives of all three germ layers in vivo. Since no iPSC colony formation or line derivation from the transduced SSEA3-negative cells was observed, this indicates that these cells possess significantly lower or even no reprogramming potential relative to the SSEA3-expressing cells. Additionally, a 10-fold enrichment of primary fibroblasts that strongly express SSEA3 results in a significantly greater efficiency (8-fold increase) of iPSC line derivation compared to the control derivation rate ($p<0.05$). The SSEA3-positive cells appeared indistinguishable, morphologically, from the SSEA3-negative fibroblasts; furthermore, expression of the SSEA3 antigen is not considered a marker of other cell types such as mesenchymal or epidermal adult stem cells.

Some embodiments of the disclosure use platelet rich plasm to activate a rare subpopulation of SSEA3 expressing cells that exist in the dermis of adult human skin. These SSEA3-expressing cells undergo a significant increase in cell number in response to injury, indicating a role in regeneration. These SSEA3-expressing regeneration-associated (SERA) cells were derived through primary cell culture, purified by fluorescence activated cell sorting (FACS) and characterized. The SERA cells demonstrated a global transcriptional state most similar to bone marrow and fat derived mesenchymal stem cells (MSCs) and the highest expressing SSEA3 expressing cells co-expressed CD105. However, these cells cannot differentiate into adipocytes, osteoblasts or chondrocytes.

In some embodiments of the disclosure, patients receiving fibroblast therapy are pretreated with $0.3\times10^6$ IU of aldesleukin daily for the purpose of increasing T regulatory cells in a synergistic manner with the existing immune modulatory activity of administration of fibroblasts, and/or exosomes derived from said fibroblast. Concentrations for clinical uses of aldesleukin could be used from the literature as described for other indications including heart failure (22), Wiskott-Aldrich syndrome (23), Graft Versus Host Disease (24,25), lupus (26), type 1 diabetes (27-29) and are incorporated by reference. In some embodiments of the disclosure, administration of low doses of IL-2 in the form of aldesleukin every day at concentrations of $0.3\times10^6$ to $3.0\times10^6$ IU IL-2 per square meter of body surface area for 8 weeks, or in other embodiments repetitive 5-day courses of $1.0\times10^6$ to $3.0\times10^6$ IU IL-2. Various types of IL-2 may be utilized. Examples of IL-2 variants, recombinant IL-2, methods of IL-2 production, methods of IL-2 purification, methods of formulation, and the like are well known in the art and can be found, for example, at least in U.S. Pat. Nos. 4,530,787, 4,569,790, 4,572,798, 4,604,377, 4,748,234, 4,853,332, 4,959,314, 5,464,939, 5,229,109, 7,514,073, and 7,569,215, each of which is herein incorporated by reference in their entirety for all purposes. In some embodiments of the disclosure, administration of estrogen is performed in order to assist in the expansion of Treg cells. The utilization of estrogen to advance expansion of Treg cells has previously been demonstrated and is incorporated by reference. For example, it is known that CD4(+)CD25(+) regulatory T cells are crucial to the maintenance of tolerance in normal individuals in augmenting FoxP3 expression in vitro and in vivo (30). Investigators showed that treatment of naive mice with estradiol (E2) increased both CD25(+) cell number and FoxP3 expression level. Further, the ability of E2 to protect against autoimmune disease (experimental autoimmune encephalomyelitis) correlated with its ability to up-regulate FoxP3, as both were reduced in estrogen receptor alpha-deficient animals. Finally, E2 treatment and pregnancy induced FoxP3 protein expression to a similar degree, suggesting that high estrogen levels during pregnancy may help to maintain fetal tolerance (31). Tolerogenic potential of estrogen, and methods of utilization of estrogen are provided in the following papers and incorporated by reference (32-62).

In some embodiments, fibroblasts, or fibroblast conditioned media is used in combination with an immune suppressive agent to augment its activity at reducing inflammation associated with multiple sclerosis. It will be known to one of skill in the art to choose from various immune suppressive agents. For example, some immune suppressive agents, such as anti-CD52 antibodies may be used when a systemic depletion of T and B cells is desired, whereas agents that concurrently stimulate T regulatory cell activity, such as Rapamycin, may be desired in other cases. The skilled practitioner is guided to several agents that are known in the art for causing immune suppression, which include cyclosporine, rapamycin, campath-1H, ATG, Prograf, anti IL-2r, MMF, FTY, LEA, cyclosporin A, diftitox, denileukin, levamisole, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, and trimetrexate), purine analogs (e.g., cladribine, fludarabine, 6-mercaptopurine, thiamiprine, and thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, and tegafur) fluocinolone, triaminolone, anecortave acetate, fluorometholone, medrysone, prednisolone, etc. In another embodiment, the use of stem cell conditioned media may be used to potentiate an existing anti-inflammatory agent. Anti-inflammatory agents may comprise one or more agents including NSAIDs, interleukin-1 antagonists, dihydroorotate synthase inhibitors, p38 MAP kinase inhibitors, TNF-α inhibitors, TNF-α sequestration agents, and methotrexate. More specifically, anti-inflammatory agents may comprise one or more of, e.g., anti-TNF-α, lysophylline, alpha 1-antitrypsin (AAT), interleukin-10 (IL-10), pentoxifylline, COX-2 inhibitors, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (eg., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), epsilon.-acetamidocaproic acid, s-adenosylmethionine, 3-amino-4-hydroxybutyric.acid, amixetrine, bendazac, benzydamine, α-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, zileuton, candelilla wax, alpha bisabolol, aloe vera, Manjistha, Guggal, kola extract, chamomile, sea whip extract, glycyrrhetic acid, glycyrrhizic acid, oil soluble licorice extract, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid.

In some embodiments of the disclosure, Wharton's jelly fibroblast cells are used as a source of immune modulatory cells. Wharton's jelly cells may be derived from umbilical cords that are obtained from healthy mothers that have no history of genetic diseases or cancer, and have been tested negative for hepatitis B/C virus, human immunodeficiency virus, Epstein-Barr virus, cytomegalovirus and syphilis in serum. Manufacturing of Wharton's jelly fibroblasts is performed in under sterile conditions, for example in a laminar flow hood. During the process of manufacturing, it is ideal for the production to occur in a class 10,000 clean production suite. Each technician properly gowns when entering in the GMP room. Before entry into the clean lab area, the technician obtains a bunny suit in the ante room. After the hood of the bunny suit is placed on, a mouth covering is put on, making sure that all hair is fully covered under the hood and mouth covering. The technician puts on a pair of sterile powder free gloves, and enters the clean lab space with the sample. Environmental monitoring is performed in the Class 10,000 clean room. The umbilical cord is washed with phosphate buffered saline (PBS) twice and then dissected with scissors into pieces approximately one cubic centimeter in volume. The tissue is subsequently plated into a culture dish in low-DMEM medium supplemented with 5-10% platelet rich plasma or fetal calf serum. Cell cultures are maintained in a humidified atmosphere with 5% CO2 at 37° C. After approximately 3 days of culture, the medium is replaced to remove the tissue and non-adherent cells, and the media is changed twice weekly thereafter. Once 80% confluence is reached, the adherent cells (passage 0) were detached with approximately 0.125% trypsin and passaged in the cell culture dish. The Wharton's jelly fibroblast cells are cultured and expanded for 4-6 passages to prepare final cell products. The cellular product is assessed for contamination, including aerobic and anaerobic bacteria, mycoplasma, HBV, HCV, HIV, EBV, CMV, syphilis, and endotoxin testing. To assess purity, cells must possess>90% expression of CD90 and CD105 and <5% CD34, CD45 and HLA-DR. Additionally, cells must have a chromosomal karyotype of UC-MSC to be normal.

For production of fibroblast cells, reagent qualification may be necessary. The qualification process begins with the vender of the reagent. The vender is qualified through our standard operating procedure. A corresponding form is completed and approval gained before a vender can be used. The Criteria identified as important in qualifying a supplier include quality of product, services offered, competitive pricing, communication, availability, how complaints are handled and the overall fit to our systems. This list is not all inclusive. Quality Systems reviews each qualification form and will approve based on the criteria stated above. Once the vender is approved, they are added to the Supplies and Services List. Associates ordering supplies including reagents use the list. Only approved venders on the list are used by associates ordering supplies involving reagents. Once the reagent arrives, it is logged on the Supplies Receipt, Inspection and Inventory Log. The form instructs the associate to complete certain information for the incoming reagent. These fields are date received, initials of receiver, name of the item, manufacturer, lot number, expiration date, package passed visual inspection, product passed visual inspection, date available for use and quantity. The COA is examined for reagents and placed in the applicable COA binder under that reagent name. These binders are retained per the record retention procedure. Once this is completed the reagent is released from quarantine and placed in the applicable area. If the reagent needs refrigerated or is to remain frozen, it is placed in the applicable storage environment. FDA or other national regulatory body-approved reagents are used if available. In some embodiments, an excipient used in the cryopreservation of the cells is Dimethyl Sulfoxide (DMSO). Each dose of fibroblast cell may be cryopreserved using 10% DMSO, or 2 mL of DMSO in a total volume of 10 mL of final product. Infusion of this amount of DMSO is well within the safety parameters for a 30 kg child; Pediatric Stem Cell Transplant SOP states that the maximum dose of DMSO is 15 mg/kg/dose. For intralymphatic, or perilymphatic administration, various amounts of cells may be used, as well as numerous lymphatic locations.

One skilled in the art knows numerous methods of cellular cryopreservation. Typically, cells are treated to a cryoprotection process, then stored frozen until needed. Once needed cells require specialized care for revival and washing to clear cryopreservative agents that may have detrimental effects on cellular function. Generally, cryopreservation requires attention be paid to three main concepts, these are: 1) The cryoprotective agent, 2) The control of the freezing rate, and 3) The temperature at which the cells will be stored at. Cryoprotective agents are well known to one skilled in the art and can include but are not limited to dimethyl sulfoxide (DMSO), glycerol, polyvinylpyrrolidine, polyethylene glycol, albumin, dextran, sucrose, ethylene glycol, i-erythritol, D-ribitol, D-mannitol, D-sorbitol, i-inositol, D-lactose, or choline chloride as described in U.S. Pat. No. 6,461,645. A method for cryopreservation of cells is DMSO at a concentration not being immediately cytotoxic to cells, under conditions which allow it to freely permeate the cell whose freezing is desired and to protect intracellular organelles by combining with water and prevent cellular damage induced from ice crystal formation. Addition of plasma at concentrations between 20-25% by volume can augment the protective effect of DMSO. After addition of DMSO, cells should be kept at temperatures below 4° C., in order to prevent DMSO mediated damage. Methods of actually inducing the cells in a state of suspended animation involve utilization of various cooling protocols. While cell type, freezing reagent, and concentration of cells are important variables in determining methods of cooling, it is generally accepted that a controlled, steady rate of cooling is optimal. There are numerous devices and apparatuses known in the field that are capable of reducing temperatures of cells for optimal cryopreservations. One such apparatus is the Thermo Electro Cryomed Freezer™ manufactured by Thermo Electron Corporation. Cells can also be frozen in CryoCyte™ containers as made by Baxter. One example of cryopreservation is as follows: $2 \times 10^6$ CD34 cells/ml are isolated from cord blood using the Isolex System™ as per manufacturer's instructions (Baxter). Cells are incubated in DMEM media with 10% DMSO and 20% plasma. Cooling is performed at 1 Celsius./minute from 0 to −80 Celsius. When cells are needed for use, they are thawed rapidly in a water bath maintained at 37 Celsius water bath and chilled immediately upon thawing. Cells are rapidly washed, either a buffer solution, or a solution containing a growth factor. Purified cells can then be used for expansion if needed. A database of stored cell information (such as donor, cell origination types, cell markers, etc.) can also be prepared, if desired.

In some embodiments of the disclosure, the fibroblast cells may be genetically altered, for example, they may be genetically modified to express, and optionally, secrete one or more immune modulatory factors. Examples of such factors include BLC, Eotaxin-1, Eotaxin-2, G-CSF, GM-CSF, I-309, ICAM-1, IL-1 ra, IL-2, IL-4, IL-5, IL-6 sR, IL-7, IL-10, IL-13, IL-16, MCP-1, M-CSF, MIG, MIP-1 alpha, MIP-1 beta, MIP-1 delta, PDGF-BB, RANTES, TIMP-1, TIMP-2, TNF alpha, TNF beta, sTNFRI, sTNFRIIAR, BDNF, bFGF, BMP-4, BMP-5, BMP-7, b-NGF, EGF, EGFR, EG-VEGF, FGF-4, FGF-7, GDF-15, GDNF, Growth Hormone, HB-EGF, HGF, IGFBP-1, IGFBP-2, IGFBP-3, IGFBP-4, IGFBP-6, IGF-1, Insulin, M-CSF R, NGF R, NT-3, NT-4, Osteoprotegerin, PDGF-AA, PlGF, SCF, SCF R, TGFalpha, TGF beta 1, TGF beta 3, VEGF, VEGFR2, VEGFR3, VEGF-D 6Ckine, Axl, BTC, CCL28, CTACK, CXCL16, ENA-78, Eotaxin-3, GCP-2, GRO, HCC-1, HCC-4, IL-9, IL-17F, IL-18 BPa, IL-28A, IL-29, IL-31, IP-10, I-TAC, LIF, Light, Lymphotactin, MCP-2, MCP-3, MCP-4, MDC, MIF, MIP-3 alpha, MIP-3 beta, MPIF-1, MSPalpha, NAP-2, Osteopontin, PARC, PF4, SDF-1 alpha, TARC, TECK, TSLP 4-1BB, ALCAM, B7-1, BCMA, CD14, CD30, CD40 Ligand, CEACAM-1, DR6, Dtk, Endoglin, ErbB3, E-Selectin, Fas, Flt-3L, GITR, HVEM, ICAM-3, IL-1 R4, IL-1 RI, IL-10 Rbeta, IL-17R, IL-2Rgamma, IL-21R, LIMPII, Lipocalin-2, L-Selectin, LYVE-1, MICA, MICB, NRG1-beta1, PDGF Rbeta, PECAM-1, RAGE, TIM-1, TRAIL R3, Trappin-2, uPAR, VCAM-1, XEDARActivin A, AgRP, Angiogenin, Angiopoietin 1, Catheprin S, CD40, Cripto-1, DAN, DKK-1, E-Cadherin, EpCAM, Fas Ligand, Fcg RIIB/C, Follistatin, Galectin-7, ICAM-2, IL-13 R1, IL-13R2, IL-17B, IL-2 Ra, IL-2 Rb, IL-23, LAP, NrCAM, PAI-1, PDGF-AB, Resistin, SDF-1 beta, sgp130, ShhN, Siglec-5, ST2, TGF beta 2, Tie-2, TPO, TRAIL R4, TREM-1, VEGF-C, VEGFR1 Adiponectin, Adipsin, AFP, ANGPTL4, B2M, BCAM, CA125, CA15-3, CEA, CRP, ErbB2, Follistatin, FSH, GRO alpha, beta HCG, IGF-1 sR, IL-1 sRII, IL-3, IL-18 Rb, IL-21, Leptin, MMP-1, MMP-2, MMP-3, MMP-8, MMP-9, MMP-10, MMP-13, NCAM-1, Nidogen-1, NSE, OSM, Procalcitonin, Prolactin, PSA, Siglec-9, TACE, Thyroglobulin, TIMP-4, TSH2B4, ADAM-9, Angiopoietin 2, APRIL, BMP-2, BMP-9, C5a, Cathepsin L, CD200, CD97, Chemerin, DcR3, FABP2, FAP, FGF-19, Galectin-3, HGF R, IFN-gammalpha/beta ?R2, IGF-2, IGF-2 R, IL-1R6, IL-24, IL-33, Kallikrein 14, Legumain, LOX-1, MBL, Neprilysin, Notch-1, NOV, Osteoactivin, PD-1, PGRP-5, Serpin A4, sFRP-3, Thrombomodulin, TLR2, TRAIL R1, Transferrin, WIF-1ACE-2, Albumin, AMICA, Angiopoietin 4, BAFF, CA19-9, CD163, Clusterin, CRTAM, CXCL14, Cystatin C, Decorin, Dkk-3, DLL1, Fetuin A, aFGF, FOLR1, Furin, GASP-1, GASP-2, GCSF R, HAI-2, IL-17B R, IL-27, LAG-3, LDL R, Pepsinogen I, RBP4, SOST, Syndecan-1, TACI, TFPI, TSP-1, TRAIL R2, TRANCE, Troponin I, uPA, VE-Cadherin, WISP-1, and RANK.

Without departing from the spirit of the disclosure, fibroblast cells of the disclosure may be optimized to possess heightened immune modulatory properties. In some embodiments this may be performed by exposure of fibroblast cells to hypoxic conditions, specifically hypoxic conditions can comprise an oxygen level of lower than 10%. In some embodiments, hypoxic conditions comprise up to about 7% oxygen. For example, hypoxic conditions can comprise up to about 7%, up to about 6%, up to about 5%, up to about 4%, up to about 3%, up to about 2%, or up to about 1% oxygen. As another example, hypoxic conditions can comprise up to 7%, up to 6%, up to 5%, up to 4%, up to 3%, up to 2%, or up to 1% oxygen. In some embodiments, hypoxic conditions comprise about 1% oxygen up to about 7% oxygen. For example, hypoxic conditions can comprise about 1% oxygen up to about 7% oxygen; about 2% oxygen up to about 7% oxygen; about 3% oxygen up to about 7% oxygen; about 4% oxygen up to about 7% oxygen; about 5% oxygen up to about 7% oxygen; or about 6% oxygen up to about 7% oxygen. As another example, hypoxic conditions can comprise 1% oxygen up to 7% oxygen; 2% oxygen up to 7% oxygen; 3% oxygen up to 7% oxygen; 4% oxygen up to 7% oxygen; 5% oxygen up to 7% oxygen; or 6% oxygen up to 7% oxygen. As another example, hypoxic conditions can comprise about 1% oxygen up to about 7% oxygen; about 1% oxygen up to about 6% oxygen; about 1% oxygen up to about 5% oxygen; about 1% oxygen up to about 4% oxygen; about 1% oxygen up to about 3% oxygen; or about 1% oxygen up to about 2% oxygen. As another example, hypoxic conditions can comprise 1% oxygen up to 7% oxygen; 1% oxygen up to 6% oxygen; 1% oxygen up to 5% oxygen; 1% oxygen up to 4% oxygen; 1% oxygen up to 3% oxygen; or 1% oxygen up to 2% oxygen. As another example, hypoxic conditions can comprise about 1% oxygen up to about 7% oxygen; about 2% oxygen up to about 6% oxygen; or about 3% oxygen up to about 5% oxygen. As another example, hypoxic conditions can comprise 1% oxygen up to 7% oxygen; 2% oxygen up to 6% oxygen; or 3% oxygen up to 5% oxygen. In some embodiments, hypoxic conditions can comprise no more than about 2% oxygen. For example, hypoxic conditions can comprise no more than 2% oxygen.

III. Fibroblast Administration

While the disclosure encompasses the generation of T regulatory cells, while in certain embodiments concurrently inducing neuroregeneration, the unanticipated discovery that administration of fibroblasts alone, and/with other agents, provides means of inducing tolerogenesis, the process of tolerogenesis, and hence, the objectives of the current disclosure, lends itself to treatment of other pathologies. Clinically, it is believed that a substantial number of pregnancy failures in the first trimester are associated with immunological causes (63). In neoplasia, transgenic expression of defined antigens on tumors leads to selective inhibition of systemic T cell responses to the specific antigens (64-66). The ability of tumors to inhibit peripheral T cell activity has been associated in numerous studies with poor prognosis (67-69). Ingestion of antigen, including the RA autoantigen collagen II (70), has been shown to induce inhibition of both T and B cell responses in a specific manner (71,72). Remission of disease in animal models of RA (73), multiple sclerosis (74), and type I diabetes (75), has been reported by oral administration of autoantigens. Anterior chamber associated immune deviation (ACAID) is a phenomena in which local implantation of antigen results in a systemic immune modulation towards the antigen. Commonly this is demonstrated by antigen-specific suppression of DTH responses after intra-chamber administration of antigen (76). Induction of ACAID has been used therapeutically in treatment of a mouse model of pulmonary inflammation: pretreatment with anterior chamber antigen injection resulted in systemic production from pulmonary damage (77).

Fibroblast cell concentrations for administration vary according to specific autoimmune condition, stage of condition, and characteristics of the patient. In some embodiments, a total dose of 0.5 million-300 million fibroblasts are administered intralymphatically, or perilymphatically, or any other suitable route (including but not limited to intravenously, subcutaneously, intrathecally, orally, intrarectally, intra-omentrally, intraventricularly, intrahepaticly, and intrarenally) to an individual in need of immune modulation, such as an individual suffering from autoimmunity, including multiple sclerosis. In particular embodiments, fibroblasts are administered at a concentration of about 10,000-2,000,000/kg per dose, such as per infusion. The dose may be 10,000-2,000,000; 10,000-1,000,000; 10,000-500,000; 10,000-250,000; 10,000-100,000; 100,000-2,000,000; 100,000-1,000,000; 100,000-500,000; 100,000-250,000; 250,000-2,000,000; 250,000-1,000,000; 250,000-500,000; 500,000-2,000,000; or 500,000-1,000,000/kg per dose, for example. The fibroblasts may be administered at a concentration of 10,000/kg per dose; 50,000/kg per dose; 100,000/kg per dose; 500,000/kg per dose; 1,000,000/kg per dose; or 2,000,000/kg per dose.

The number of administrations of cells to an individual will depend upon the factors described herein at least in part and may be optimized using routine methods in the art. In specific embodiments, a single administration is required. In other embodiments, a plurality of administration of cells is required. It should be appreciated that the system is subject to variables, such as the particular need of the individual, which may vary with time and circumstances, the rate of loss of the cellular activity as a result of loss of cells or activity of individual cells, and the like. Therefore, it is expected that each individual could be monitored for the proper dosage, and such practices of monitoring an individual are routine in the art.

Additionally, cell concentrations or types of cells useful for the practice of the disclosure may be determined by assessment of production of immune modulatory products. One family of immune modulatory products includes the prostanoids. Prostanoids include any of a group of complex fatty acids derived from arachidonic acid, including the prostaglandins, prostanoic acid, and the thromboxanes. Examples of prostanoids of interest include Prostaglandin A, Prostaglandin B, Prostaglandin C, Prostaglandin D, Prostaglandin D2, Prostaglandin E1, Prostaglandin E2, Prostaglandin E2G, Prostaglandin F-alpha, Prostaglandin G, Prostaglandin I, Prostaglandin 12, Prostaglandin J, Prostaglandin K, Thromboxane A2, and Thromboxane B2. In one particular embodiment, the concentration of PGE-2 is utilized as a marker of immune suppressive activity of administered cells, of particular interest, the concentration of PGE-2 produced by fibroblast stem cells is utilized as a marker of immune suppressive activity of fibroblast stem cells, said immune suppressive activity is associated with inhibition of autoimmune activity.

The frequency of fibroblast cell injection may be performed once, or multiple times, including for example once a week, or monthly, or yearly. Factors that come into consideration include the stage of autoimmune disease, as well as patient specific factors. Factors of consideration include the amount of T cell autoreactivity that is ongoing as part of the autoimmune process. Specifically T cell autoreactivity may be assessed utilizing CD8 tetramers and flow cytometry, with said tetramers bearing autoantigen. Quantification of autoreactive T cell numbers may be performed by flow cytometry. Activation may be assessed by culture with said autoantigen and assessment of proliferation or cytokine production. Methods are known in the art for assessment of proliferation and autoantigen specific cytokine production such as thymidine incorporation and ELISPOT, respectively. Additional methods of assessing cytokine production include ELISA, Luminex, RT-PCR, Northern Blot and microarrays. Cytokines of interest include ones of specific relevance to autoimmunity including BLC, Eotaxin-1, Eotaxin-2, G-CSF, GM-CSF, 1-309, ICAM-1, IFN-gamma, IL-1 alpha, IL-1 beta, IL-1 ra, IL-2, IL-4, IL-5, IL-6, IL-6 sR, IL-7, IL-8, IL-10, IL-11, IL-12 p40, IL-12 p'70, IL-13, IL-15, IL-16, IL-17, MCP-1, M-CSF, MIG, MIP-1 alpha, MIP-1 beta, MIP-1 delta, PDGF-BB, RANTES, TIMP-1, TIMP-2, TNF alpha, TNF beta, sTNFRI, sTNFRIIAR, BDNF, bFGF, BMP-4, BMP-5, BMP-7, b-NGF, EGF, EGFR, EG-VEGF, FGF-4, FGF-7, GDF-15, GDNF, Growth Hormone, HB-EGF, HGF, IGFBP-1, IGFBP-2, IGFBP-3, IGFBP-4, IGFBP-6, IGF-1, Insulin, M-CSF R, NGF R, NT-3, NT-4, Osteoprotegerin, PDGF-AA, PlGF, SCF, SCF R, TGFalpha, TGF beta 1, TGF beta 3, VEGF, VEGFR2, VEGFR3, VEGF-D 6Ckine, Axl, BTC, CCL28, CTACK, CXCL16, ENA-78, Eotaxin-3, GCP-2, GRO, HCC-1, HCC-4, IL-9, IL-17F, IL-18 BPa, IL-28A, IL-29, IL-31, IP-10, I-TAC, LIF, Light, Lymphotactin, MCP-2, MCP-3, MCP-4, MDC, MIF, MIP-3 alpha, MIP-3 beta, MPIF-1, MSPalpha, NAP-2, Osteopontin, PARC, PF4, SDF-1 alpha, TARC, TECK, TSLP 4-1BB, ALCAM, B7-1, BCMA, CD14, CD30, CD40 Ligand, CEACAM-1, DR6, Dtk, Endoglin, ErbB3, E-Selectin, Fas, Flt-3L, GITR, HVEM, ICAM-3, IL-1 R4, IL-1 RI, IL-10 Rbeta, IL-17R, IL-2Rgamma, IL-21R, LIMPII, Lipocalin-2, L-Selectin, LYVE-1, MICA, MICB, NRG1-beta1, PDGF Rbeta, PECAM-1, RAGE, TIM-1, TRAIL R3, Trappin-2, uPAR, VCAM-1, XEDARActivin A, AgRP, Angiogenin, Angiopoietin 1, Angiostatin, Catheprin S, CD40, Cripto-1, DAN, DKK-1, E-Cadherin, EpCAM, Fas Ligand, Fcg RIIB/C, Follistatin, Galectin-7, ICAM-2, IL-13 R1, IL-13R2, IL-17B, IL-2 Ra, IL-2 Rb, IL-23, LAP, NrCAM, PAI-1, PDGF-AB, Resistin, SDF-1 beta, sgp130, ShhN, Siglec-5, ST2, TGF beta 2, Tie-2, TPO, TRAIL R4, TREM-1, VEGF-C, VEGFR1 Adiponectin, Adipsin, AFP, ANGPTL4, B2M, BCAM, CA125, CA15-3, CEA, CRP, ErbB2, Follistatin, FSH, GRO alpha, beta HCG, IGF-1 sR, IL-1 sRII, IL-3, IL-18 Rb, IL-21, Leptin, MMP-1, MMP-2, MMP-3, MMP-8, MMP-9, MMP-10, MMP-13, NCAM-1, Nidogen-1, NSE, OSM, Procalcitonin, Prolactin, PSA, Siglec-9, TACE, Thyroglobulin, TIMP-4, TSH2B4, ADAM-9, Angiopoietin 2, APRIL, BMP-2, BMP-9, C5a, Cathepsin L, CD200, CD97, Chemerin, DcR3, FABP2, FAP, FGF-19, Galectin-3, HGF R, IFN-gammalpha/beta ?R2, IGF-2, IGF-2 R, IL-1R6, IL-24, IL-33, Kallikrein 14, Legumain, LOX-1, MBL, Neprilysin, Notch-1, NOV, Osteoactivin, PD-1, PGRP-5, Serpin A4, sFRP-3, Thrombomodulin, TLR2, TRAIL R1, Transferrin, WIF-LACE-2, Albumin, AMICA, Angiopoietin 4, BAFF, CA19-9, CD163, Clusterin, CRTAM, CXCL14, Cystatin C, Decorin, Dkk-3, DLL1, Fetuin A, aFGF, FOLR1, Furin, GASP-1, GASP-2, GCSF R, HAI-2, IL-17B R, IL-27, LAG-3, LDL R, Pepsinogen I, RBP4, SOST, Syndecan-1, TALI, TFPI, TSP-1, TRAIL R2, TRANCE, Troponin I, uPA, VE-Cadherin, WISP-1, and RANK.

One of skill in the art would understand that given the propensity of fibroblast cells to inhibit inflammatory mediators such as TNF-alpha, IFN-gamma, and stimulate anti-inflammatory proteins such as IL-4 and PSG1, in one aspect of the disclosure, fibroblast cells would be administered at a concentration and frequency to inhibit ongoing inflammation. For example, patients with higher levels of autoreactive T cells producing IFN-gamma would be treated with a higher number of fibroblast cells, and/or at a higher frequency of administration as compared to patients with lower autoreactive T cells. Dosing may also be determined based on clinical characteristics such as stage of the disease.

IV. Kits of the Disclosure

Any of the cellular and/or non-cellular compositions described herein or similar thereto may be comprised in a kit. In a non-limiting example, one or more reagents for use in methods for preparing cellular therapy may be comprised in a kit. Such reagents may include cells, IFN-gamma, platelet rich plasma, platelet lysate, one or more angiogenic factors, one or more growth factors, vector(s) one or more costimulatory factors, media, enzymes, buffers, nucleotides, salts, primers, and so forth. The kit may comprise any protein listed in the disclosure. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, or may be a substrate with multiple compartments for a desired reaction.

Some components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile acceptable buffer and/or other diluent.

In specific embodiments, reagents and materials include primers for amplifying desired sequences, nucleotides, suitable buffers or buffer reagents, salt, and so forth, and in some cases the reagents include apparatus or reagents for isolation of a particular desired cell(s).

In particular embodiments, there are one or more apparatuses in the kit suitable for extracting one or more samples from an individual. The apparatus may be a syringe, fine needles, scalpel, and so forth.

EXAMPLES

The following examples are included to demonstrate particular embodiments of the invention. It should be appreciated by those of skill in the art that the techniques disclosed in the examples that follow represent techniques discovered by the inventors to function well in the practice of the methods of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Fibroblasts are Superior to MSC for Treatment of Multiple Sclerosis

Adult male Lewis rats (9-10 weeks of age, 200-250 g) were assigned to four groups: normal control group (n=12), BM-MSC group (n=12), Adipose MSC group (n=12), and Fibroblast group (n=12). Experimental autoimmune encephalomyelitis (EAE) was induced by subcutaneous injection of guinea pig spinal cord homogenate (GPSCH) emulsified at a 1:1 ratio with complete Freund adjuvant (CFA) containing heat killed *Mycobacterium tuberculosis*. Each rat received an intraperitoneal injection of 300 ng Pertussis toxin (Sigma-Aldrich, St. Louis, MO, USA) in 0.1 ml distilled water immediately after the subcutaneous injection and again 48 h later. Cells where injected at a concentration of 1 million cells per rat intravenously subsequent to administration of GPSCH. The clinical manifestations of EAE were assessed daily until the time of sacrifice. Disease severity was scored on a 5-point scale: 0=no signs, 1=partial loss of tail tonicity, 2=loss of tail tonicity, 3=unsteady gait and mild paralysis, 4=hind limb paralysis and incontinence, and 5=moribund or death. Disease scoring was performed by pathologists blinded to treatment conditions. Rats treated with fibroblasts had a lower EAE severity score than controls and both MSC groups (FIG. 1).

Example 2

Cytokine Manipulation by Fibroblasts Associated with Reduction of EAE

Figure 2:
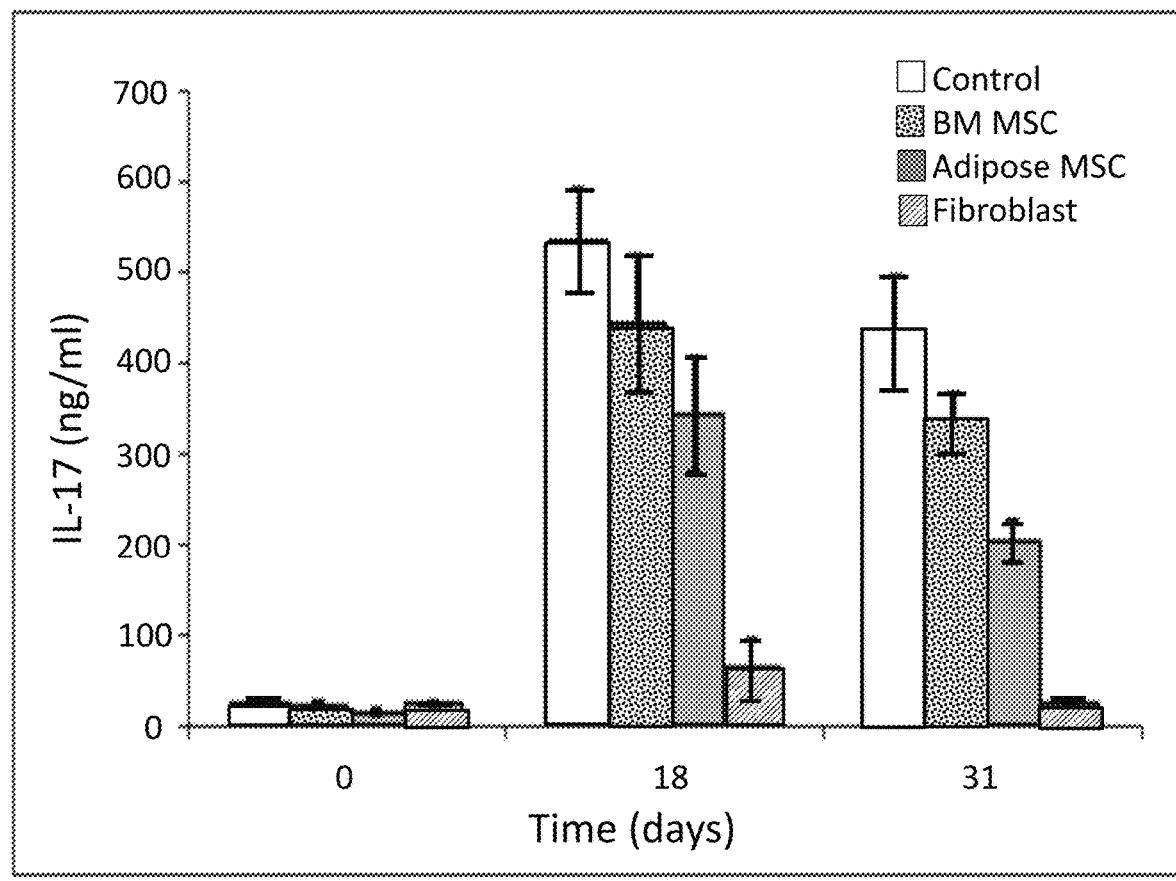
FIG. 2 shows IL-17 levels in EAE rats that were administered with a vehicle control, BM-MSC, Adipose MSC, or fibroblasts; in the groupings of four bars, the order from left to right is control, BM-MSC, Adipose MSC, and fibroblasts.
Figure 3:
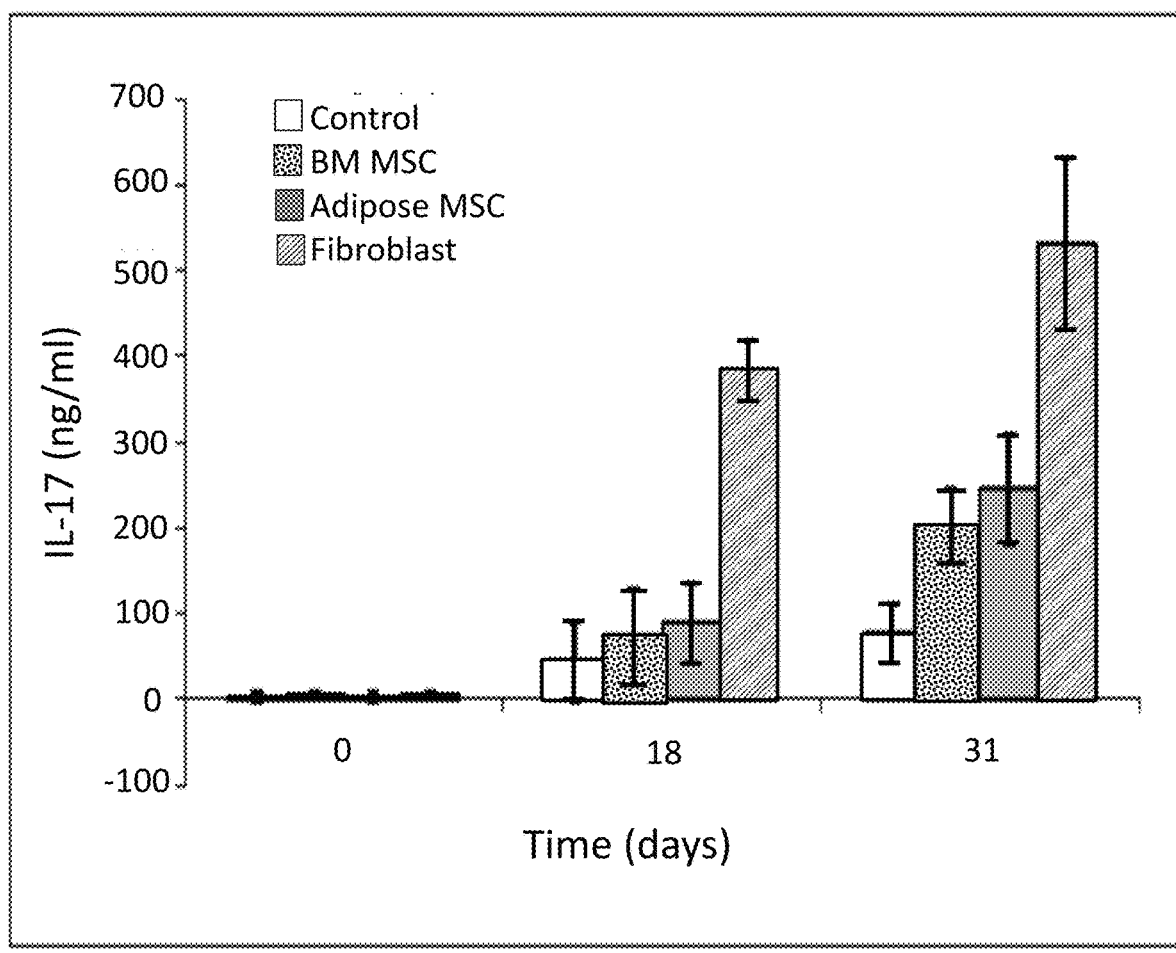
FIG. 3 shows IL-10 levels in EAE rats that were administered with a vehicle control, BM-MSC, Adipose MSC, or fibroblasts; in the groupings of four bars, the order from left to right is control, BM-MSC, Adipose MSC, and fibroblasts.

Blood samples were taken at the indicated days and cytokines analyzed by ELISA after purification of plasma. As observed, fibroblasts induced a more potent reduction in IL-17 (FIG. 2) and augmentation of IL-10 (FIG. 3) compared to other mesenchymal stem cells.

Example 3

Enhancement of Neurogenesis and Remyelination by Administration of Fibroblasts

Figure 4:
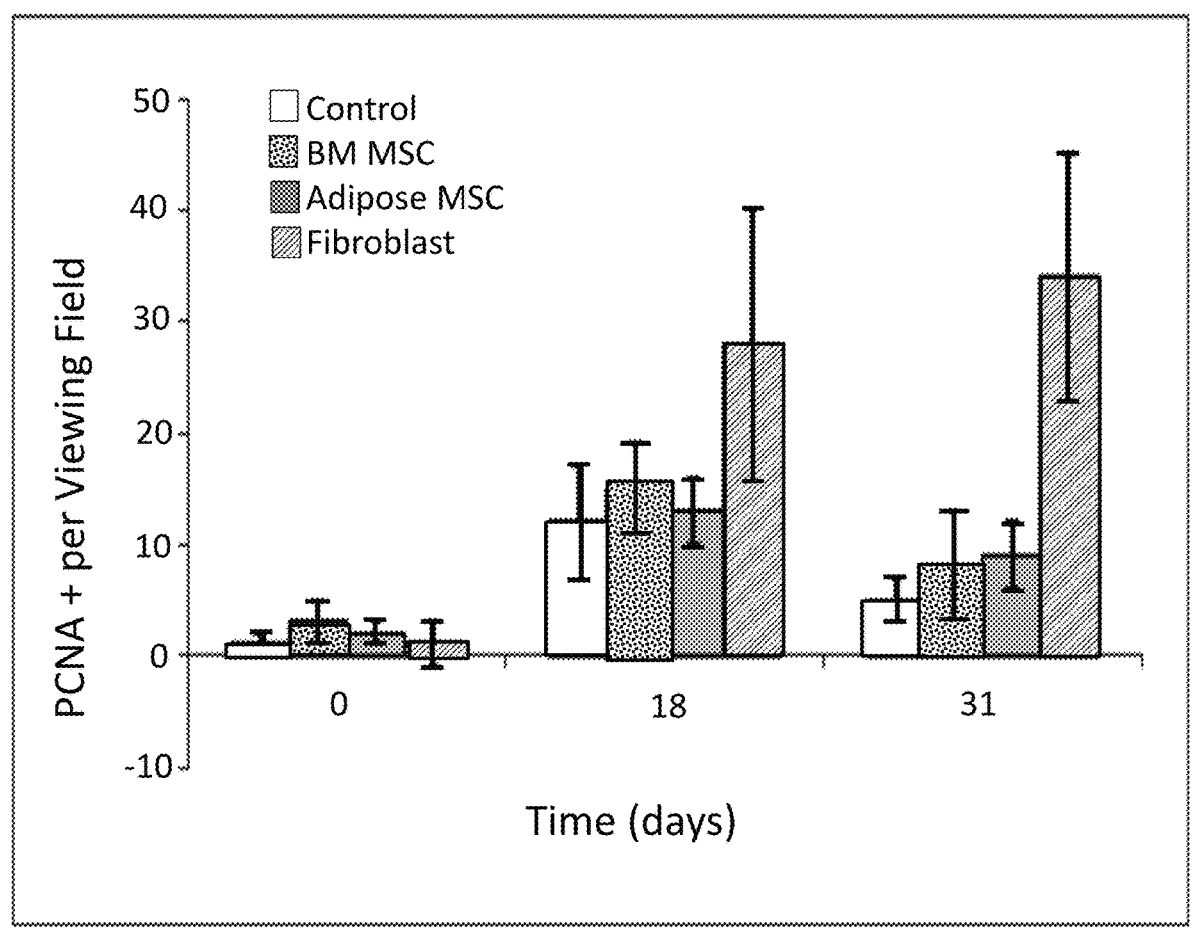
FIG. 4 shows neuroregeneration levels in EAE rats that were administered with a vehicle control, BM-MSC, Adipose MSC, or fibroblasts; in the groupings of four bars, the order from left to right is control, BM-MSC, Adipose MSC, and fibroblasts.
Figure 5:
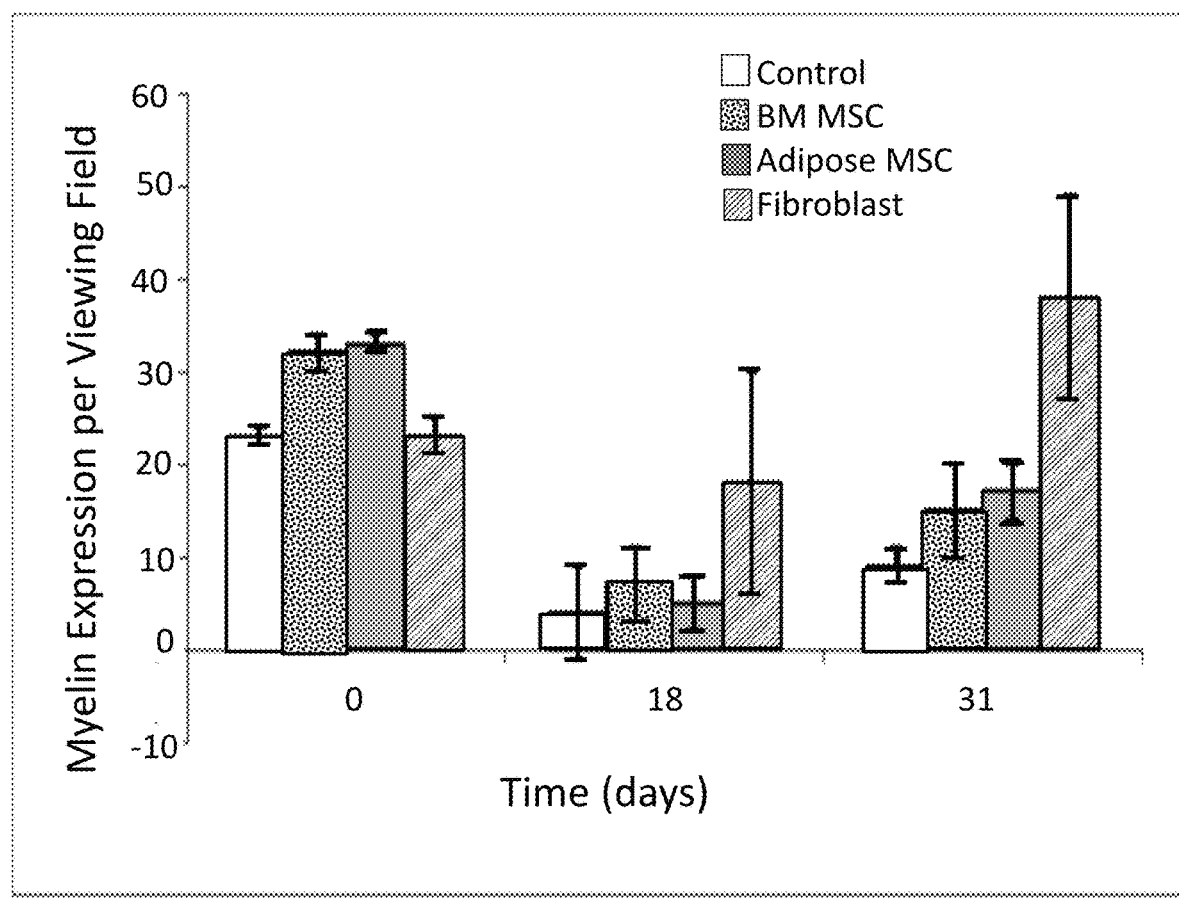
FIG. 5 shows remyelination levels in EAE rats that were administered with a vehicle control, BM-MSC, Adipose MSC, or fibroblasts.

Animals suffering from EAE were sacrificed at the indicated time points and assessment of neuronal regeneration and myelination where performed by immunohistology. As observed, regenerative (FIG. 4) and remyelination (FIG. 5) processes were present in the fibroblast treated mice at a superior level compared to mesenchymal stem cell treated animals.

Example 4

Mechanistic Experiments

Adult male Lewis rats (9-10 weeks of age, 200-250 g) were assigned to four groups: normal control group (n=12), Fibroblasts and anti-CD25 antibody administered once every 6 days (n=12), Fibroblasts and anti-CD25 antibody administered once every 3 days (n=12), and Fibroblast alone group (n=12). Experimental autoimmune encephalomyelitis (EAE) was induced by subcutaneous injection of guinea pig spinal cord homogenate (GPSCH) emulsified at a 1:1 ratio with complete Freund adjuvant (CFA) containing heat killed *Mycobacterium tuberculosis*. Each rat received an intraperitoneal injection of 300 ng Pertussis toxin (Sigma-Aldrich, St. Louis, MO, USA) in 0.1 ml distilled water immediately after the subcutaneous injection and again 48 h later. One million cells per rat where administered after administration of GPSCH.

Figure 6:
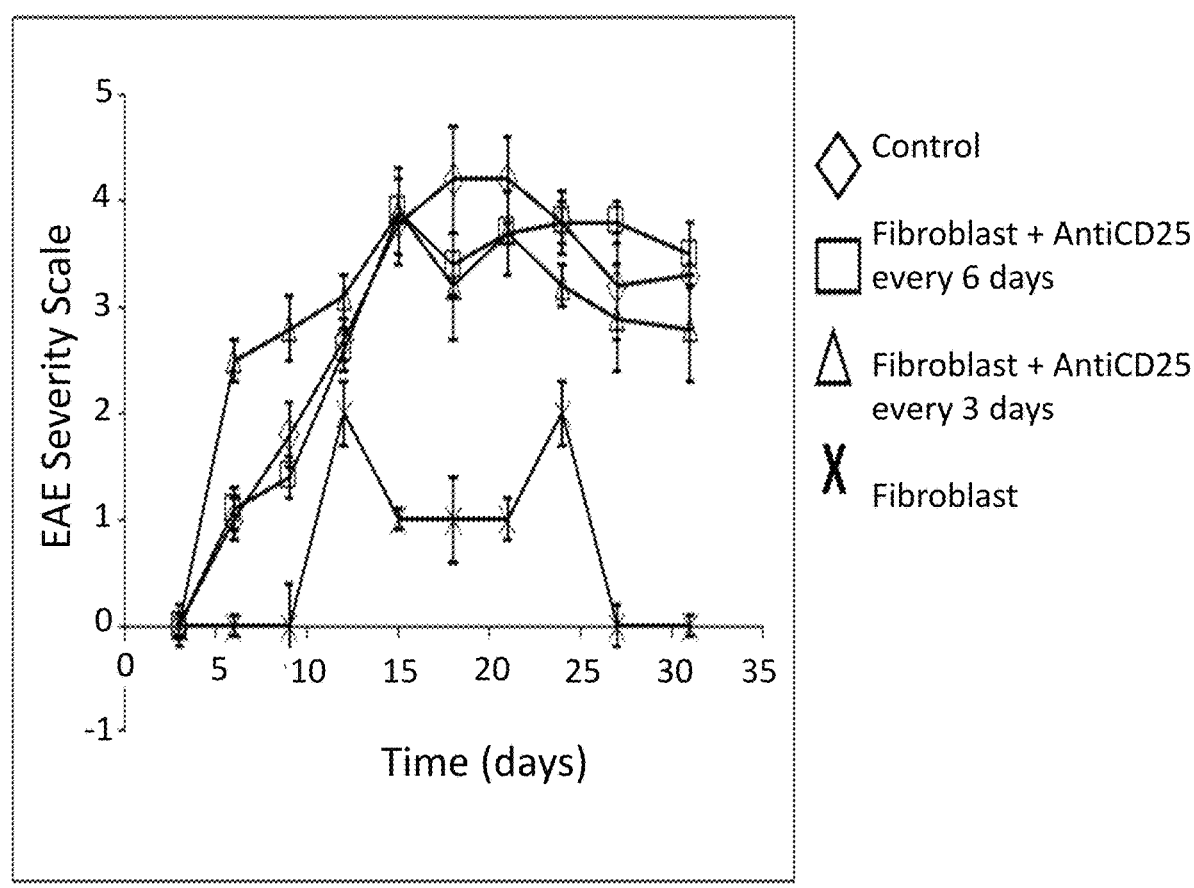
FIG. 6 shows clinical manifestations of experimental autoimmune encephalomyelitis EAE in rats that were administered with a vehicle control, fibroblasts alone, fibroblasts co-administered with an anti-CD25 antibody every 6 days, or, fibroblasts co-administered with an anti-CD25 antibody every 3 days.

The clinical manifestations of EAE were assessed daily until the time of sacrifice. Disease severity was scored on a 5-point scale: 0=no signs, 1=partial loss of tail tonicity, 2=loss of tail tonicity, 3=unsteady gait and mild paralysis, 4=hind limb paralysis and incontinence, and 5=moribund or death. Disease scoring was performed by pathologists blinded to treatment conditions. Rats treated with fibroblasts alone had a lower EAE severity score than controls and anti-CD25 groups (FIG. 6).

Example 5

Figure 7:
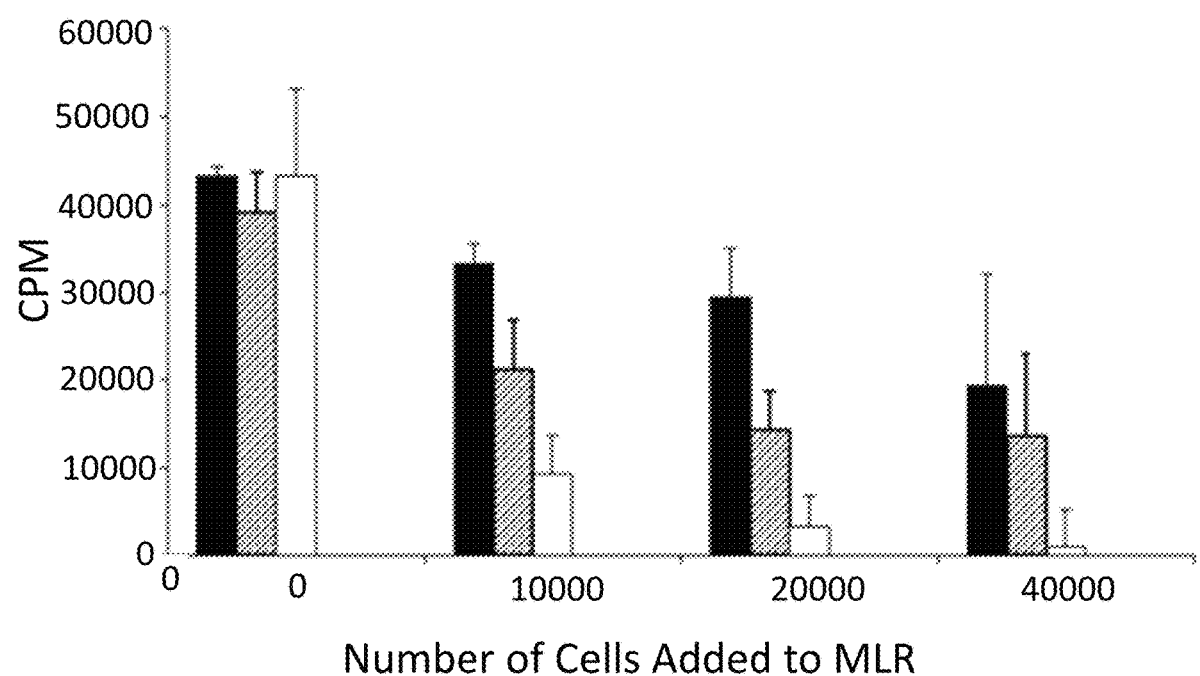
FIG. 7 shows co-culture of myelin basic protein reactive CD4 T cells and fibroblasts at indicated amounts. Proliferation was quantified. Black bars=T cells and myelin basic protein and IL-2. Grey bars=T cells and myelin basic protein without IL-2. White bars=T cells alone.

Fibroblasts Directly Suppress Proliferation of Myelin Basic Protein Reactive T Cells CD4 myelin basic protein reactive T cell clones were generated by culture of recombinant myelin basic protein (Abcam, 10 µg/mL) with irradiated autologous peripheral blood mononuclear cells in the presence of interleukin-2 (10 IU/mL). After establishment of clones, the CD4 cells were cultured with irradiated dendritic cells in the presence of the indicated number of fibroblasts added to the culture. Proliferation of cells was quantified by tritiated thymidine incorporation. Increasing fibroblast concentrations reduced the proliferation of myelin basic protein reactive T cells (FIG. 7).

Example 6

Fibroblasts Stimulate Expansion of Treg Cells Specific for Myelin Basic Protein

Figure 8:
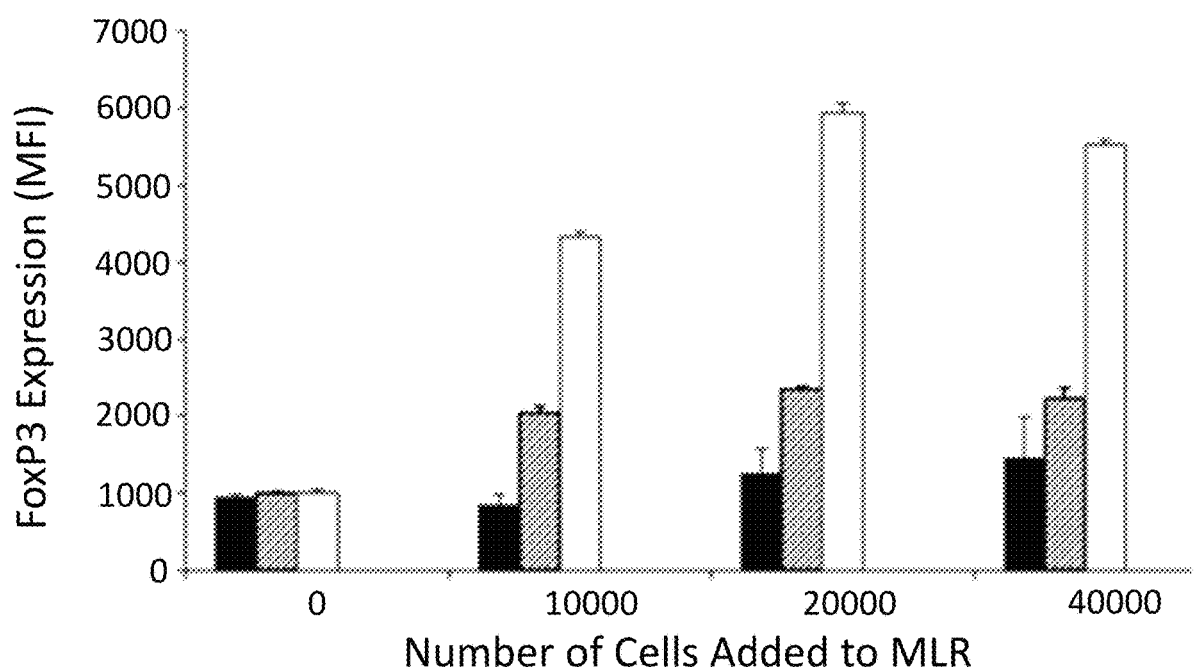
FIG. 8 shows co-culture of myelin basic protein reactive CD4 T cells and fibroblasts at indicated amounts. FoxP3 expression was quantified. White bars=T cells and myelin basic protein and IL-2. Grey bars=T cells and myelin basic protein without IL-2. Black bars=T cells alone.

CD4 myelin basic protein reactive T cell clones were generated by culture of recombinant myelin basic protein (Abcam, 10 µg/mL) with irradiated autologous peripheral blood mononuclear cells in the presence of interleukin-2 (10 IU/mL). After establishment of clones, the CD4 cells were cultured with irradiated dendritic cells in the presence of the indicated number of fibroblasts added to the culture. Increasing fibroblasts concentrations increased FoxP3 expression (FIG. 8).

REFERENCES

1. Adams, N. M., O'Sullivan, T. E., Geary, C. D., Karo, J. M., Amezquita, R. A., Joshi, N. S., Kaech, S. M., and Sun, J. C. (2016) NK Cell Responses Redefine Immunological Memory. *Journal of immunology* 197, 2963-2970
2. Serre, L., Fazilleau, N., and Guerder, S. (2015) Central tolerance spares the private high-avidity CD4(+) T-cell repertoire specific for an islet antigen in NOD mice. *European journal of immunology* 45, 1946-1956
3. Enouz, S., Carrie, L., Merkler, D., Bevan, M. J., and Zehn, D. (2012) Autoreactive T cells bypass negative selection and respond to self-antigen stimulation during infection. *The Journal of experimental medicine* 209, 1769-1779
4. Aluvihare, V. R., Kallikourdis, M., and Betz, A. G. (2004) Regulatory T cells mediate maternal tolerance to the fetus. *Nat Immunol* 5, 266-271
5. Somerset, D. A., Zheng, Y., Kilby, M. D., Sansom, D. M., and Drayson, M. T. (2004) Normal human pregnancy is associated with an elevation in the immune suppressive CD25+ CD4+ regulatory T-cell subset. *Immunology* 112, 38-43
6. Campos-Mora, M., Contreras-Kallens, P., Galvez-Jiron, F., Rojas, M., Rojas, C., Refisch, A., Cerda, O., and Pino-Lagos, K. (2019) CD4+Foxp3+ T Regulatory Cells Promote Transplantation Tolerance by Modulating Effector CD4+ T Cells in a Neuropilin-1-Dependent Manner. *Front Immunol* 10, 882
7. Lalfer, M., Chappert, P., Carpentier, M., Urbain, D., Davoust, J. M., and Gross, D. A. (2019) Foxp3(+) Regulatory and Conventional CD4(+) T Cells Display Similarly High Frequencies of Alloantigen-Reactive Cells. *Front Immunol* 10, 521
8. Wang, K., Song, Z. L., Wu, B., Zhou, C. L., Liu, W., and Gao, W. (2019) Different phenotypes of CD4(+)CD25(+) Foxp3(+) regulatory T cells in recipients post liver transplantation. *Int Immunopharmacol* 69, 194-201
9. Herrera-Gomez, F., Del Aguila, W., Tejero-Pedregosa, A., Adler, M., Padilla-Berdugo, R., Maurtua-Briseno-Meiggs, A., Pascual, J., Pascual, M., San Segundo, D., Heidt, S., Alvarez, F. J., Ochoa-Sangrador, C., and Lambert, C. (2018) The number of FoxP3 regulatory T cells in the circulation may be a predictive biomarker for kidney transplant recipients: A multistage systematic review. *Int Immunopharmacol* 65, 483-492
10. Leung, C. S., Yang, K. Y., Li, X., Chan, V. W., Ku, M., Waldmann, H., Hori, S., Tsang, J. C. H., Lo, Y. M. D., and Lui, K. O. (2018) Single-cell transcriptomics reveal that PD-1 mediates immune tolerance by regulating proliferation of regulatory T cells. *Genome Med* 10, 71
11. Zhu, X., Yang, P., Zhou, H., Li, B., Huang, X., Meng, Q., Wang, L., and Kijlstra, A. (2007) CD4+CD25+Tregs express an increased LAG-3 and CTLA-4 in anterior chamber-associated immune deviation. *Graefes Arch Clin Exp Ophthalmol* 245, 1549-1557
12. Zhang, H., Yang, P., Zhou, H., Meng, Q., and Huang, X. (2008) Involvement of Foxp3-expressing CD4+CD25+ regulatory T cells in the development of tolerance induced by transforming growth factor-beta2-treated antigen-presenting cells. *Immunology* 124, 304-314
13. He, H., Yang, P., Jiang, L., Zhang, J., Zhao, C., Chen, L., Lin, X., Zhou, H., and Kijlstra, A. (2008) Upregulation of CD94 on CD8+ T cells in anterior chamber-associated immune deviation. *BMC Immunol* 9, 53
14. Saban, D. R., Cornelius, J., Masli, S., Schwartzkopff, J., Doyle, M., Chauhan, S. K., Peck, A. B., and Grant, M. B. (2008) The role of ACAID and CD4+CD25+FOXP3+ regulatory T cells on CTL function against MHC alloantigens. *Mol Vis* 14, 2435-2442
15. Hori, J., Taniguchi, H., Wang, M., Oshima, M., and Azuma, M. (2010) GITR ligand-mediated local expansion of regulatory T cells and immune privilege of corneal allografts. *Invest Ophthalmol Vis Sci* 51, 6556-6565
16. Ji, S. X., Yin, X. L., and Yang, P. Z. (2011) Effect of CD4(+)CD25(+) regulatory T cells in the development of anterior chamber-associated immune deviation. *Int J Ophthalmol* 4, 19-25
17. Zhang, Y., Zhang, M., Zhao, S., Li, X., Jia, Z., Zhang, L., Han, Z. C., and Zhang, X. (2013) Effects of human umbilical cord-derived mesenchymal stem cells on anterior chamber-associated immune deviation. *Int Immunopharmacol* 15, 114-120
18. Yan, F., Cai, L., Hui, Y., Chen, S., Meng, H., and Huang, Z. (2014) Tolerogenic dendritic cells suppress murine corneal allograft rejection by modulating CD28/CTLA-4 expression on regulatory T cells. *Cell Biol Int* 38, 835-848
19. Wang, T., Shi, W., Fan, T., Wan, X., Chen, Y. H., and Ruan, Q. (2016) c-Rel is Required for the Induction of pTregs in the Eye but Not in the Gut Mucosa. *Immunol Invest* 45, 776-786
20. Kunishige, T., Taniguchi, H., Terada, M., Akiba, H., Yagita, H., Abe, R., and Hori, J. (2016) Protective Role of ICOS and ICOS Ligand in Corneal Transplantation and in Maintenance of Immune Privilege. *Invest Ophthalmol Vis Sci* 57, 6815-6823
21. Zenclussen, A. C., Gerlof, K., Zenclussen, M. L., Sollwedel, A., Bertoja, A. Z., Ritter, T., Kotsch, K., Leber, J., and Volk, H. D. (2005) Abnormal T-cell reactivity against paternal antigens in spontaneous abortion: adoptive transfer of pregnancy-induced CD4+CD25+ T regulatory cells prevents fetal rejection in a murine abortion model. *Am J Pathol* 166, 811-822
22. Zhao, T. X., Kostapanos, M., Griffiths, C., Arbon, E. L., Hubsch, A., Kaloyirou, F., Helmy, J., Hoole, S. P., Rudd, J. H. F., Wood, G., Burling, K., Bond, S., Cheriyan, J., and Mallat, Z. (2018) Low-dose interleukin-2 in patients with stable ischaemic heart disease and acute coronary syndromes (LILACS): protocol and study rationale for a randomised, double-blind, placebo-controlled, phase I/II clinical trial. *BMJ Open* 8, e022452
23. Jyonouchi, S., Gwafila, B., Gwalani, L. A., Ahmad, M., Moertel, C., Holbert, C., Kim, J. Y., Kobrinsky, N., Roy-Ghanta, S., and Orange, J. S. (2017) Phase I trial of low-dose interleukin 2 therapy in patients with Wiskott-Aldrich syndrome. *Clin Immunol* 179, 47-53
24. Asano, T., Matsuoka, K. I., Iyama, S., Ohashi, K., Inamoto, Y., Ohwada, C., Murata, M., Satake, A., Yoshida, C., Nakase, K., Mori, Y., and Tanimoto, M. (2016) Phase I/IIa Study of Low Dose Subcutaneous Interleukin-2 (IL-2) for Treatment of Refractory Chronic Graft Versus Host Disease. *Acta Med Okayama* 70, 429-433
25. Kennedy-Nasser, A. A., Ku, S., Castillo-Caro, P., Hazrat, Y., Wu, M. F., Liu, H., Melenhorst, J., Barrett, A. J., Ito, S., Foster, A., Savoldo, B., Yvon, E., Carrum, G., Ramos, C. A., Krance, R. A., Leung, K., Heslop, H. E., Brenner, M. K., and Bollard, C. M. (2014) Ultra low-dose IL-2 for GVHD prophylaxis after allogeneic hematopoietic stem cell transplantation mediates expansion of regulatory T cells without diminishing antiviral and antileukemic activity. *Clin Cancer Res* 20, 2215-2225

26. Mizui, M., and Tsokos, G. C. (2016) Low-Dose IL-2 in the Treatment of Lupus. *Curr Rheumatol Rep* 18, 68

27. Todd, J. A., Evangelou, M., Cutler, A. J., Pekalski, M. L., Walker, N. M., Stevens, H. E., Porter, L., Smyth, D. J., Rainbow, D. B., Ferreira, R. C., Esposito, L., Hunter, K. M., Loudon, K., Irons, K., Yang, J. H., Bell, C. J., Schuilenburg, H., Heywood, J., Challis, B., Neupane, S., Clarke, P., Coleman, G., Dawson, S., Goymer, D., Anselmiova, K., Kennet, J., Brown, J., Caddy, S. L., Lu, J., Greatorex, J., Goodfellow, I., Wallace, C., Tree, T. I., Evans, M., Mander, A. P., Bond, S., Wicker, L. S., and Waldron-Lynch, F. (2016) Regulatory T Cell Responses in Participants with Type 1 Diabetes after a Single Dose of Interleukin-2: A Non-Randomised, Open Label, Adaptive Dose-Finding Trial. *PLoS Med* 13, e1002139

28. Pham, M. N., von Herrath, M. G., and Vela, J. L. (2015) Antigen-Specific Regulatory T Cells and Low Dose of IL-2 in Treatment of Type 1 Diabetes. *Front Immunol* 6, 651

29. Waldron-Lynch, F., Kareclas, P., Irons, K., Walker, N. M., Mander, A., Wicker, L. S., Todd, J. A., and Bond, S. (2014) Rationale and study design of the Adaptive study of IL-2 dose on regulatory T cells in type 1 diabetes (DILT1D): a non-randomised, open label, adaptive dose finding trial. *BMJ Open* 4, e005559

30. Wei, C., Mei, J., Tang, L., Liu, Y., Li, D., Li, M., and Zhu, X. (2016) 1-Methyl-tryptophan attenuates regulatory T cells differentiation due to the inhibition of estrogen-IDO1-MRC2 axis in endometriosis. *Cell Death Dis* 7, e2489

31. Polanczyk, M. J., Carson, B. D., Subramanian, S., Afentoulis, M., Vandenbark, A. A., Ziegler, S. F., and Offner, H. (2004) Cutting edge: estrogen drives expansion of the CD4+CD25+ regulatory T cell compartment. *J Immunol* 173, 2227-2230

32. Tai, P., Wang, J., Jin, H., Song, X., Yan, J., Kang, Y., Zhao, L., An, X., Du, X., Chen, X., Wang, S., Xia, G., and Wang, B. (2008) Induction of regulatory T cells by physiological level estrogen. *J Cell Physiol* 214, 456-464

33. Offner, H. (2004) Neuroimmunoprotective effects of estrogen and derivatives in experimental autoimmune encephalomyelitis: therapeutic implications for multiple sclerosis. *J Neurosci Res* 78, 603-624

34. Polanczyk, M. J., Hopke, C., Huan, J., Vandenbark, A. A., and Offner, H. (2005) Enhanced FoxP3 expression and Treg cell function in pregnant and estrogen-treated mice. *J Neuroimmunol* 170, 85-92

35. Offner, H., and Vandenbark, A. A. (2005) Congruent effects of estrogen and T-cell receptor peptide therapy on regulatory T cells in EAE and MS. *Int Rev Immunol* 24, 447-477

36. Polanczyk, M. J., Hopke, C., Vandenbark, A. A., and Offner, H. (2006) Estrogen-mediated immunomodulation involves reduced activation of effector T cells, potentiation of Treg cells, and enhanced expression of the PD-1 costimulatory pathway. *J Neurosci Res* 84, 370-378

37. Offner, H., and Polanczyk, M. (2006) A potential role for estrogen in experimental autoimmune encephalomyelitis and multiple sclerosis. *Ann N Y Acad Sci* 1089, 343-372

38. Polanczyk, M. J., Hopke, C., Vandenbark, A. A., and Offner, H. (2007) Treg suppressive activity involves estrogen-dependent expression of programmed death-1 (PD-1). *Int Immunol* 19, 337-343

39. Sinha, S., Kaler, L. J., Proctor, T. M., Teuscher, C., Vandenbark, A. A., and Offner, H. (2008) IL-13-mediated gender difference in susceptibility to autoimmune encephalomyelitis. *J Immunol* 180, 2679-2685

40. Huber, S. A. (2008) Coxsackievirus B3-induced myocarditis: infection of females during the estrus phase of the ovarian cycle leads to activation of T regulatory cells. *Virology* 378, 292-298

41. Wang, C., Dehghani, B., Li, Y., Kaler, L. J., Proctor, T., Vandenbark, A. A., and Offner, H. (2009) Membrane estrogen receptor regulates experimental autoimmune encephalomyelitis through up-regulation of programmed death 1. *J Immunol* 182, 3294-3303

42. Wang, C., Dehghani, B., Li, Y., Kaler, L. J., Vandenbark, A. A., and Offner, H. (2009) Oestrogen modulates experimental autoimmune encephalomyelitis and interleukin-17 production via programmed death 1. *Immunology* 126, 329-335

43. Zhang, B., Subramanian, S., Dziennis, S., Jia, J., Uchida, M., Akiyoshi, K., Migliati, E., Lewis, A. D., Vandenbark, A. A., Offner, H., and Hum, P. D. (2010) Estradiol and G1 reduce infarct size and improve immunosuppression after experimental stroke. *J Immunol* 184, 4087-4094

44. Lin, X. G., Zhou, Q., Wang, L., Gao, Y., Zhang, W. N., Luo, Z. L., Chen, B. C., Chen, Z. H., and Chang, S. (2010) Pregnancy estrogen drives the changes of T-lymphocyte subsets and cytokines and prolongs the survival of H-Y skin graft in murine model. *Chin Med J (Engl)* 123, 2593-2599

45. Subramanian, S., Yates, M., Vandenbark, A. A., and Offner, H. (2011) Oestrogen-mediated protection of experimental autoimmune encephalomyelitis in the absence of Foxp3+ regulatory T cells implicates compensatory pathways including regulatory B cells. *Immunology* 132, 340-347

46. Valor, L., Teijeiro, R., Aristimuno, C., Faure, F., Alonso, B., de Andres, C., Tejera, M., Lopez-Lazareno, N., Fernandez-Cruz, E., and Sanchez-Ramon, S. (2011) Estradiol-dependent perforin expression by human regulatory T-cells. *Eur J Clin Invest* 41, 357-364

47. Luo, C. Y., Wang, L., Sun, C., and Li, D. J. (2011) Estrogen enhances the functions of CD4(+)CD25(+) Foxp3(+) regulatory T cells that suppress osteoclast differentiation and bone resorption in vitro. *Cell Mol Immunol* 8, 50-58

48. Shirshev, S. V., Orlova, E. G., Zamorina, S. A., and Nekrasova, I. V. (2011) Influence of reproductive hormones on the induction of CD4(+)CD25 (bright)Foxp (3+) regulatory T cells. *Dokl Biol Sci* 440, 343-346

49. Tyagi, A. M., Srivastava, K., Mansoori, M. N., Trivedi, R., Chattopadhyay, N., and Singh, D. (2012) Estrogen deficiency induces the differentiation of IL-17 secreting Th17 cells: a new candidate in the pathogenesis of osteoporosis. *PLoS One* 7, e44552

50. Bodhankar, S., Vandenbark, A. A., and Offner, H. (2012) Oestrogen treatment of experimental autoimmune encephalomyelitis requires 17 beta-oestradiol-receptor-positive B cells that up-regulate PD-1 on CD4+ Foxp3+ regulatory T cells. *Immunology* 137, 282-293

51. Cho, J., Kim, L., Li, Z., Rose, N. R., Talor, M. V., and Njoku, D. B. (2013) Sex bias in experimental immune-mediated, drug-induced liver injury in BALB/c mice: suggested roles for Tregs, estrogen, and IL-6. *PLoS One* 8, e61186

52. Haghmorad, D., Amini, A. A., Mahmoudi, M. B., Rastin, M., Hosseini, M., and Mahmoudi, M. (2014) Pregnancy level of estrogen attenuates experimental autoimmune encephalomyelitis in both ovariectomized and pregnant C57BL/6 mice through expansion of Treg and Th2 cells. *J Neuroimmunol* 277, 85-95

53. Zhang, J., Lapato, A., Bodhankar, S., Vandenbark, A. A., and Offner, H. (2015) Treatment with IL-10 producing B cells in combination with E2 ameliorates EAE severity and decreases CNS inflammation in B cell-deficient mice. *Metab Brain Dis* 30, 1117-1127

54. Spanier, J. A., Nashold, F. E., Mayne, C. G., Nelson, C. D., and Hayes, C. E. (2015) Vitamin D and estrogen synergy in Vdr-expressing CD4(+) T cells is essential to induce Helios(+)FoxP3(+) T cells and prevent autoimmune demyelinating disease. *J Neuroimmunol* 286, 48-58

55. Gourdy, P., Bourgeois, E. A., Levescot, A., Pham, L., Riant, E., Ahui, M. L., Damotte, D., Gombert, J. M., Bayard, F., Ohlsson, C., Arnal, J. F., and Herbelin, A. (2016) Estrogen Therapy Delays Autoimmune Diabetes and Promotes the Protective Efficiency of Natural Killer T-Cell Activation in Female Nonobese Diabetic Mice. *Endocrinology* 157, 258-267

56. Huber, S. (2015) ERbeta and ERalpha Differentially Regulate NKT and Vgamma4(+) T-cell Activation and T-regulatory Cell Response in Coxsackievirus B3 Infected Mice. *J Clin Cell Immunol* 6, 1-9

57. Aggelakopoulou, M., Kourepini, E., Paschalidis, N., and Panoutsakopoulou, V. (2016) ERbeta in CD4+ T Cells Is Crucial for Ligand-Mediated Suppression of Central Nervous System Autoimmunity. *J Immunol* 196, 4947-4956

58. Haghmorad, D., Salehipour, Z., Nosratabadi, R., Rastin, M., Kokhaei, P., Mahmoudi, M. B., Amini, A. A., and Mahmoudi, M. (2016) Medium-dose estrogen ameliorates experimental autoimmune encephalomyelitis in ovariectomized mice. *J Immunotoxicol* 13, 885-896

59. Mohammad, I., Starskaia, I., Nagy, T., Guo, J., Yatkin, E., Vaananen, K., Watford, W. T., and Chen, Z. (2018) Estrogen receptor alpha contributes to T cell-mediated autoimmune inflammation by promoting T cell activation and proliferation. *Sci Signal* 11

60. Gamier, L., Laffont, S., Lelu, K., Yogev, N., Waisman, A., and Guery, J. C. (2018) Estrogen Signaling in Bystander Foxp3(neg) CD4(+) T Cells Suppresses Cognate Th17 Differentiation in Trans and Protects from Central Nervous System Autoimmunity. *J Immunol* 201, 3218-3228

61. Iannello, A., Rolla, S., Maglione, A., Ferrero, G., Bardina, V., Inaudi, I., De Mercanti, S., Novelli, F., D'Antuono, L., Cardaropoli, S., Todros, T., Turrini, M. V., Cordioli, C., Puorro, G., Marsili, A., Lanzillo, R., Brescia Morra, V., Cordero, F., De Bortoli, M., Durelli, L., Visconti, A., Cutrupi, S., and Clerico, M. (2018) Pregnancy Epigenetic Signature in T Helper 17 and T Regulatory Cells in Multiple Sclerosis. *Front Immunol* 9, 3075

62. Shirshev, S. V., Nekrasova, I. V., Gorbunova, 0. L., and Orlova, E. G. (2019) Regulation of Recombinase Rag-1 Expression by Female Sex Steroids in Treg and Th17 Lymphocytes: Role of Oncostatin M. *Dokl Biochem Biophys* 484, 73-77

63. Clark, D. A. (2003) Is there any evidence for immunologically mediated or immunologically modifiable early pregnancy failure? *J Assist Reprod Genet* 20, 63-72

64. Ney, J. T., Schmidt, T., Kurts, C., Zhou, Q., Eckert, D., Felsher, D. W., Schorle, H., Knolle, P., Tuting, T., Barchet, W., Buttner, R., Limmer, A., and Gutgemann, I. (2009) Autochthonous liver tumors induce systemic T cell tolerance associated with T cell receptor down-modulation. *Hepatology* 49, 471-481

65. Cheung, A. F., Dupage, M. J., Dong, H. K., Chen, J., and Jacks, T. (2008) Regulated expression of a tumor-associated antigen reveals multiple levels of T-cell tolerance in a mouse model of lung cancer. *Cancer Res* 68, 9459-9468

66. Bai, A., Higham, E., Eisen, H. N., Wittrup, K. D., and Chen, J. (2008) Rapid tolerization of virus-activated tumor-specific CD8+ T cells in prostate tumors of TRAMP mice. *Proc Natl Acad Sci USA* 105, 13003-13008

67. Whiteside, T. L. (2004) Down-regulation of zeta-chain expression in T cells: a biomarker of prognosis in cancer? *Cancer Immunol Immunother* 53, 865-878

68. Whiteside, T. L. (1999) Signaling defects in T lymphocytes of patients with malignancy. *Cancer Immunol Immunother* 48, 346-352

69. Reichert, T. E., Strauss, L., Wagner, E. M., Gooding, W., and Whiteside, T. L. (2002) Signaling abnormalities, apoptosis, and reduced proliferation of circulating and tumor-infiltrating lymphocytes in patients with oral carcinoma. *Clin Cancer Res* 8, 3137-3145

70. Park, K. S., Park, M. J., Cho, M. L., Kwok, S. K., Ju, J. H., Ko, H. J., Park, S. H., and Kim, H. Y. (2009) Type II collagen oral tolerance; mechanism and role in collagen-induced arthritis and rheumatoid arthritis. *Mod Rheumatol*

71. Womer, K. L., Magee, C. C., Najafian, N., Vella, J. P., Milford, E. L., Sayegh, M. H., and Carpenter, C. B. (2008) A pilot study on the immunological effects of oral administration of donor major histocompatibility complex class II peptides in renal transplant recipients. *Clin Transplant* 22, 754-759

72. Faria, A. M., and Weiner, H. L. (2006) Oral tolerance: therapeutic implications for autoimmune diseases. *Clin Dev Immunol* 13, 143-157

73. Thompson, H. S., Harper, N., Bevan, D. J., and Staines, N. A. (1993) Suppression of collagen induced arthritis by oral administration of type II collagen: changes in immune and arthritic responses mediated by active peripheral suppression. *Autoimmunity* 16, 189-199

74. Song, F., Gienapp, I. E., Shawler, T., Guan, Z., and Whitacre, C. C. (2004) The thymus plays a role in oral tolerance induction in experimental autoimmune encephalomyelitis. *Ann N Y Acad Sci* 1029, 402-404

75. Hanninen, A., and Harrison, L. C. (2004) Mucosal tolerance to prevent type 1 diabetes: can the outcome be improved in humans? *Rev Diabet Stud* 1, 113-121

76. Streilein, J. W., and Niederkorn, J. Y. (1985) Characterization of the suppressor cell(s) responsible for anterior chamber-associated immune deviation (ACAID) induced in BALB/c mice by P815 cells. *J Immunol* 134, 1381-1387

77. Katagiri, K., Zhang-Hoover, J., Mo, J. S., Stein-Streilein, J., and Streilein, J. W. (2002) Using tolerance induced via the anterior chamber of the eye to inhibit Th2-dependent pulmonary pathology. *J Immunol* 169, 84-89

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of correcting or ameliorating one or more abnormalities associated with multiple sclerosis in an individual, comprising the steps of: a) administering an effective amount of a population of fibroblasts to the individual at a concentration and frequency sufficient to correct or ameliorate said one or more abnormalities, wherein the said one or more abnormalities associated with multiple sclerosis comprises abnormally high levels of interleukin-17, abnormally low levels of interleukin-10, abnormally low levels of proliferation of endogenous stem cells in the brain, or a combination thereof.

2. The method of claim 1, wherein said abnormally high levels of interleukin-17 comprise plasma levels over 50%, 60%, 70%, 80%, or 90%, higher than those found in an age-matched healthy control.

3. The method of claim 2, wherein said levels of interleukin-17 are assessed in peripheral blood or cerebral spinal fluid.

4. The method of claim 1, wherein said abnormally low levels of interleukin-10 comprise plasma levels less than 50%, 60%, 70%, 80%, or 90%, of the level found in an age-matched healthy control.

5. The method of claim 1, wherein said levels of interleukin-10 are assessed in peripheral blood.

6. The method of claim 1, wherein said levels of interleukin-10 are assessed in mononuclear cells from peripheral blood.

7. The method of claim 1, wherein said levels of interleukin-10 are assessed in CD4 cells from peripheral blood.

8. The method of claim 1, wherein said levels of interleukin-10 are assessed in Th17 cells from peripheral blood.

9. The method of claim 1, wherein said endogenous stem cells in the brain are oligodendrocytes.

10. The method of claim 1, wherein said endogenous stem cells in the brain are neuronal progenitor cells.

11. The method of claim 1, wherein said endogenous stem cells in the brain are found in the dentate gyrus.

12. The method of claim 1, wherein said endogenous stem cells in the brain are found in the subventricular zone.

13. The method of claim 1, wherein said abnormally low levels of endogenous brain stem cell proliferation is 50% lower than those found in an age-matched healthy control.

14. The method of claim 1, wherein said levels abnormally low levels of endogenous brain stem cell proliferation is assessed by functional MRI.

15. The method of claim 1, wherein said fibroblasts are derived from tissue selected from the group consisting of skin, adipose tissue, bone marrow, umbilical cord, Wharton's Jelly, Omentum, peripheral blood, mobilized peripheral blood, and a combination thereof.

16. The method of claim 15, wherein mobilization of peripheral blood to form the mobilized peripheral blood is performed by a step of administration of agents to the individual selected from the group consisting of G-CSF, GM-CSF, flt-3 ligand, mozibil, hyperbaric oxygen, ozone therapy, and a combination thereof.

17. The method of claim 1, wherein said fibroblasts express markers selected from the group consisting of extracellular vimentin, Cyclin D2, Snail, E-cadherin, SOX-2, CD105, CD90, CD29, CD73, Wt1, and a combination thereof.

18. The method of claim 1, wherein said fibroblasts are autologous.

19. The method of claim 1, wherein said fibroblasts are allogeneic.

20. The method of claim 19, wherein said fibroblasts are treated with oxytocin.

21. The method of claim 20, wherein oxytocin is administered to said fibroblasts in vitro for a period of 1 minute to 4 weeks.

22. The method of claim 21, wherein oxytocin is administered to said fibroblasts in vitro for a period of 2 hours to 1 week.

23. The method of claim 21, wherein oxytocin is administered to said fibroblasts in vitro for a period of 24 hours to 72 hours.

24. The method of claim 20, wherein said oxytocin is administered to said fibroblasts at a concentration of 10 nM-10 μM.

25. The method of claim 20, wherein said oxytocin is administered to said fibroblasts at a concentration of 100 nM-1 μM.

26. The method of claim 20, wherein said fibroblasts are assessed for ability to suppress the Th3 production of TGF-beta subsequent to cell to cell contact between the fibroblasts and Th3 cells.

27. The method of claim 1, wherein the fibroblasts are unmodified.

28. The method of claim 1, wherein the method additionally comprises the step of exposing the fibroblasts to hypoxic conditions prior to administration.

29. The method of claim 28, wherein the fibroblasts are exposed to an oxygen level lower than 10%, 9%, 8%, 7%, 6%, 5%, 4%, 3%, 2% or 1%.

30. The method of claim 1, wherein the fibroblasts express SSEA3.

31. The method of claim 1, further comprising adjusting said concentration and/or frequency based on response of said individual.

* * * * *

UNITED STATES PATENT AND TRADEMARK OFFICE
CERTIFICATE OF CORRECTION

PATENT NO. : 11,878,037 B2
APPLICATION NO. : 16/887720
DATED : January 23, 2024
INVENTOR(S) : Pete O'Heeron and Thomas Ichim It is certified that error appears in the above-identified patent and that said Letters Patent is hereby corrected as shown below:

In the Claims

In Claim 14, Column 35, Line 53, please replace "said levels abnormally low levels" with --said abnormally low levels-- therefore.

Signed and Sealed this
Twentieth Day of February, 2024

Katherine Kelly Vidal
Director of the United States Patent and Trademark Office